(12) United States Patent
Gagnon

(10) Patent No.: US 9,890,205 B2
(45) Date of Patent: Feb. 13, 2018

(54) CHROMATOGRAPHIC PURIFICATION OF IMMUNOGLOBULIN G PREPARATIONS WITH PARTICLES HAVING MULTIMODAL FUNCTIONALITIES

(71) Applicant: AGENCY FOR SCIENCE, TECHNOLOGY AND RESEARCH, Connexis (SG)

(72) Inventor: Peter Gagnon, Centros (SG)

(73) Assignee: AGENCY FOR SCIENCE, TECHNOLOGY AND RESEARCH, Singapore (SG)

(*) Notice: Subject to any disclaimer, the term of this patent is extended or adjusted under 35 U.S.C. 154(b) by 328 days.

(21) Appl. No.: 14/555,060

(22) Filed: Nov. 26, 2014

(65) Prior Publication Data
US 2015/0183852 A1 Jul. 2, 2015

Related U.S. Application Data

(63) Continuation of application No. PCT/SG2013/000031, filed on Jan. 21, 2013.

(60) Provisional application No. 61/653,913, filed on May 31, 2012.

(51) Int. Cl.
| | | |
|---|---|---|
| *C07K 16/00* | (2006.01) | |
| *C07K 16/16* | (2006.01) | |
| *C07K 1/18* | (2006.01) | |
| *C07K 16/22* | (2006.01) | |
| *B01D 15/36* | (2006.01) | |
| *C07K 1/16* | (2006.01) | |
| C07K 16/24 | (2006.01) | |
| C07K 16/32 | (2006.01) | |

(52) U.S. Cl.
CPC ............ *C07K 16/00* (2013.01); *B01D 15/363* (2013.01); *C07K 1/16* (2013.01); *C07K 1/165* (2013.01); *C07K 1/18* (2013.01); *C07K 16/22* (2013.01); *C07K 16/241* (2013.01); *C07K 16/32* (2013.01)

(58) Field of Classification Search
None
See application file for complete search history.

(56) References Cited

U.S. PATENT DOCUMENTS

| | | | | |
|---|---|---|---|---|
| 5,429,746 A * | 7/1995 | Shadle | ................. | B01D 15/327 |
| | | | | 210/635 |
| 5,559,250 A | 9/1996 | Cook et al. | | |
| 7,001,550 B2 | 2/2006 | Van Reis | | |
| 8,067,182 B2 * | 11/2011 | Kelley | ................. | B01D 15/30 |
| | | | | 435/7.1 |
| 8,435,779 B2 * | 5/2013 | Connolly | ............. | A61L 2/0088 |
| | | | | 435/183 |
| 2005/0233959 A1 * | 10/2005 | Chada | ................. | A61K 38/20 |
| | | | | 514/44 R |
| 2007/0244305 A1 * | 10/2007 | Parkkinen | ............. | A61L 2/0011 |
| | | | | 530/390.1 |
| 2008/0193981 A1 | 8/2008 | Fahrner et al. | | |
| 2009/0047723 A1 * | 2/2009 | Jensen | ........... | C12Y 304/21021 |
| | | | | 435/219 |
| 2012/0282654 A1 * | 11/2012 | Yao | ....................... | B01D 15/362 |
| | | | | 435/69.6 |
| 2013/0273607 A1 * | 10/2013 | O'Connor | ............. | C07K 1/145 |
| | | | | 435/69.6 |

FOREIGN PATENT DOCUMENTS

| | | | | |
|---|---|---|---|---|
| CN | 1311797 | 9/2001 | | |
| CN | 101306200 | 11/2008 | | |
| CN | 102286099 | 12/2011 | | |
| JP | 6-66793 | 3/1994 | | |
| WO | WO 99/64462 | 12/1999 | | |
| WO | 2005082937 A2 | 9/2005 | | |
| WO | 2006047340 | 5/2006 | | |
| WO | 2007117490 A2 | 10/2007 | | |
| WO | 2007136327 A1 | 11/2007 | | |
| WO | WO 2008/091740 A2 | 7/2008 | | |
| WO | WO 2009017491 A1 * | 2/2009 | ............... | C07K 1/18 |
| WO | 2010019493 | 2/2010 | | |
| WO | 2010048183 A1 | 4/2010 | | |
| WO | 2011080698 A1 | 7/2011 | | |

(Continued)

OTHER PUBLICATIONS

Liu et al. "Recovery and purification process development for monoclonal antibody production" mAbs 2:5, 480-499, 2010.*
Persson et al. "Purification of Antibody and Antibody-Fragment from E. coli homogenate using 6,9-Diamino-2-ethoxyacridine lactate as preciptaiton agent" Biotechnology and Bioengineering, 87(3), 2004.*
Gan et al. "Characteriziation and removal of aggregates formed by nonspecific interaction of IgM monoclonal antibodies with chromatin catabolites during cell culture production" J. of Chromatography A 1291 (2013) 33-40.*

(Continued)

*Primary Examiner* — Daniel E Kolker
*Assistant Examiner* — James Rogers
(74) *Attorney, Agent, or Firm* — Pillsbury Winthrop Shaw Pittman LLP

(57) ABSTRACT

A method of purifying a sample containing a desired protein includes the steps of (i) providing a packed chromatographic column having positively charged porous particles, (ii) equilibrating the column to the conditions to which the desired protein in the sample is to elute, (iii) contacting the sample with the packed chromatographic column such that the sample volume applied to the packed chromatographic column is less than or equal to the interparticle space of the positively charged porous particles within the packed chromatographic column, (iv) eluting the desired protein from the packed chromatographic column, where the desired protein is in a purer state and in the conditions to which the packed chromatographic column was equilibrated; where the desired protein is an antibody, an antibody fragment, an antibody derivative, or an antibody fusion protein.

86 Claims, 6 Drawing Sheets

(56) References Cited

FOREIGN PATENT DOCUMENTS

| WO | WO 2012/013930 | 2/2012 |
|----|----------------|--------|
| WO | WO 2012/015912 | 2/2012 |

OTHER PUBLICATIONS

European Office Action dated Dec. 21, 2015 for Appln. No. 13797544.7.

Akcasu et al., "5-Hydroxytryptamine in Cerebrospinal Fluid," Nature vol. 187, pp. 324 (1960).

Bresolin et al., "A new process of IgG purification by negative chromatography: Adsorption aspects of human serum proteins onto -aminodecyl-agarose," Journal of Chromatography B, 878 (2010) 2087-2093.

Burns et al., "Effect of Solution pH on Protein Transport Through Ultrafiltration Membranes," Biotechnology and Bioengineering, vol. 64, No. 1, Jul. 5, 1999, pp. 27-37.

Christensen et al., "Simple separation of DNA in antibody purification," Protein Expression and Purifications 37 (2004) 468-471.

Cordes et al., "Precipitation of Nucleic Acids with Poly(ethyleneimine)" Biotechnol. Prog. 19980, 6, 283-285.

de Souza et al., "Purification of human IgG by negative chromatography on -aminohexyl-agarose," Journal of Chromatography B, 878 (2010) 557-566.

Dissing et al., "Integrated removal of nucleic acids and recovery of LDH from homogenate of beef heart by affinity precipitation," Bioseparation 7: 221-229, 1999.

Eriksson et al., "MAb Contaminant Removal with a Multimodal Anion Exchanger" bioprocessintl.com /downstream-processing/ chromatography/mab-contaminant-removal-with-amultimodal-anion-exchanger-183607/ 7 pages, 2009.

Gagnon et al., "Dissociation and fractionation of heavy and light chains from IgG monoclonal antibodies," Journal of Chromatography A, 1218 (2011) 2402-2404.

Gagnon "Dissociation of Antibody—Contaminant Complexes With Hydroxyapatite," Trends & Developments in BioProcess Technology, Winter 2010/2011 BioProcessing Journal, pp. 14-24.

Glynn, "Process-Scale Precipitation of Impurities in Mammalian Cell Culture Broth," Process Scale Purification of Antibodies (2009) pp. 309-324.

Hunter et al., "Protein adsorption on novel acrylamido-based polymeric ion-exchangers I. Morphology and equilibrium adsorption," Journal of Chromatography A, 897 (2000) 65-80.

Hunter et al., "Protein adsorption on novel acrylamido-based polymeric ion exchangers II. Adsorption rates and column behavior," Journal of Chromatography A, 897 (2000) 81-97.

Hunter et al., "Protein adsorption on novel acrylamido-based polymeric ion-exchangers III. Salt concentration effects and elution behavior," Journal of Chromatography A, 930 (2001) 79-93.

Hunter et al., "P rotein adsorption on novel acrylamido-based polymeric ion-exchangers IV. Effects of protein size on adsorption capacity and rate," Journal of Chromatography A, 971 (2002) 105-116.

Kejnovsky et al., "DNA extraction by zinc," Nucleic Acids Research, 1997, vol. 25, No. 9, 1870-1871.

Luhrs et al., "Evicting hitchhiker antigens from purified antibodies," Journal of Chromatography B, 877 (2009) 1543-1552.

Ma et al., "Using precipitation by polyamines as an alternative to chromatographic separation in antibody purification processes," Journal of Chromatography B, 878 (2010) 798-806.

Matsuzawa et al., "Study on DNA precipitation with a cationic polymer PAC (poly aluminuim chloride)," Nucleic Acids Research Supplement No. 3, 2003, 163-164.

Mechetner et al., "The effects of hitchhiker antigens co-eluting with affinity-purified research antibodies," Journal of Chromatography B, 879 (2011) 2583-2594.

Mehta et al., "Purifying Therapeutic Monoclonal Antibodies," Society for Biological Engineering, 2009, S14-S20.

Ongkudon et al., "Analysis of Selective Metal-Salt-induced Endotoxin Precipitation in Plasmid DNA Purification Using Improved Limulus Amoebocyte Lysate Assay and Central Composite Design," Analytical Chemistry, vol. 83, No. 1, Jan. 1, 2011, pp. 391-397.

Peram et al., "Monoclonal Antibody Purification Using Cationic Polyelectrolytes: An Alternative to Column Chromatography," Biotechnol. Prog., 2010, vol. 26, No. 5, 1322-1331.

Reis et al., "Bioprocess membrane technology," Journal of Membrane Science 297 (2007) 16-50.

Reis et al., "High-performance tangential flow filtration using charged membranes," Journal of Membrane Science 159 (1999) 133±142.

Shukla et al., "Host Cell Protein Clearance During Protein A Choromatography: Development of an IMproved Column Wash Step," Biotechnol. Prog. 2008, 24, 1115-1121.

Thommes et al., "Alternatives to Packed-bed Chromatography for Antibody Extraction and Purification," Process Scale Purification of Antibodies 2009, pp. 293-308.

Chinese Office Action dated Oct. 8, 2016 in corresponding Chinese Patent Application No. 201380040418.9 (10 pages).

Japanese Office Action dated Nov. 9, 2016 in corresponding Japanese Patent Application No. 2015-514962 (7 pages).

Bolton et al., "Effect of Membrane Charge on High Performance Tangential Flow Filtration Separations", Advances in Filtration and Separation Technology, (1999) vol. 13A, pp. 537-544.

Ho, Steven C. L. et al., "IRES-mediated Tricistronic vectors for enhancing generation of high monoclonal antibody expressing CHO cell lines", Journal of Biotechnology, Jan. 2012, vol. 157, pp. 130-139.

Gagnon, Pete et al., "Cooperative multimodal retention of IgG, fragments, and aggregates on hydroxyapatite", Journal of Separation Science, Nov. 2009, vol. 32, pp. 3857-3865.

Bhut Bharat V et al: 11 The role of polymer nanolayer architecture on the separation performance of anion-exchange membrane adsorbers: I. Protein separations., Biotechnology and Bioengineering Nov. 2011, vol. 108, No. 11, Nov. 2011 (Nov. 2011), pp. 2645-2653.

Noh et al: "Volumetric interpretation of protein adsorption: Ion-exchange adsorbent capacity, protein pi, and interaction energetics", Biomaterials, Elsevier Science Publishers BV., Barking, GB, vol. 29, No. 13, Mar. 4, 2008 (Mar. 4, 2008), pp. 2033-2048.

Sommerfeld et al: "Challenges in biotechnology production-generic processes and process optimization for monoclonal antibodies", Chemical Engineering and Processing, Elsevier Sequoia, Lausanne, CH, vol. 44, No. 10, Oct. 1, 2005 (Oct. 1, 2005), pp. 1123-1137.

Tugcu Nihal et al: "Maximizing productivity of chromatography steps for purification of monoclonal antibodies", Biotechnology and Bioengineering, Wiley & Sons, Hoboken, NJ, US, vol. 99, No. 3, Feb. 15, 2008 (Feb. 15, 2008), pp. 599-613.

Van Qi et al: "Chromatography on DEAE ion-exchange and Protein G affinity columns in tandem for the separation and purification of proteins", Journal of Biochemical and Biophysical Methods, vol. 49, No. 1-3, Oct. 1, 2001 (Oct. 1, 2001), pp. 263-273.

European Office Action dated Jul. 21, 2017 for European Patent Application No. 13797544.7.

Official Action dated Sep. 5, 2017, in Japanese Patent Application No. 2015-514962.

* cited by examiner

CHROMATOGRAPHIC PURIFICATION OF IMMUNOGLOBULIN G PREPARATIONS WITH PARTICLES HAVING MULTIMODAL FUNCTIONALITIES

CROSS-REFERENCE TO RELATED APPLICATIONS

This application is a continuation of PCT/SG2013/000031 filed Jan. 21, 2013, which claims the priority of U.S. Provisional Application No. 61/653,913, filed May 31, 2012 the disclosures of which are incorporated herein by reference in their entireties.

FIELD OF THE INVENTION

This invention relates to methods for the purification of proteins, and more particularly to the purification of antibodies and fragments, fragmentary constructs, and Fc-fusion proteins derived from antibodies. It further relates to methods for reducing levels of antibody aggregates (homoaggregates) and antibody-contaminant complexes (heteroaggregates) from samples of antibodies and fragments, as well as viruses, DNA, and endotoxins. It further relates to the integration of these capabilities with other purification methods to achieve the desired level of final purification.

BACKGROUND OF THE INVENTION

Solid materials with charged surfaces are used widely in the field of protein purification generally, and for antibody purification in particular. These materials commonly include so-called ion exchangers, which are usually employed in either of two application formats. In bind-elute mode, the sample and ion exchanger are equilibrated to conditions that allow the antibody to bind. Contaminants that interact weakly or not at all with the charged surface fail to bind and are eliminated. Contaminants that interact more strongly than the antibody bind more strongly. After washing to remove unbound contaminants, the column may be eluted by increasing the salt concentration. This permits fractionation of bound species in increasing order of the strength of their interaction with the ion exchanger, thereby achieving a high degree of antibody purification. Inflow-through mode, the sample and ion exchanger are both equilibrated to conditions that prevent the antibody from binding. Species that interact more strongly with the ion exchanger than the antibody are bound and thereby removed, but species that bind more weakly than the antibody flow through with it and persist as contaminants. With human, humanized or chimeric IgG monoclonal antibodies, most bind-elute applications are conducted on cation exchangers (negatively charged surface). Most flow-through applications are conducted on anion exchangers (positively charged surface). Both modes are performed on charged surfaces presented in a variety of solid phase architectures, including porous or non-porous particles packed in columns, or added directly to large volume aqueous samples, or on monoliths or membranes. These different architectures confer different flow properties, capacity, and resolution, but the defining chemical features of flow-through or bind-elute chromatography are constant regardless of physical format. Both methods rely on the equilibration of the ion exchanger and sample to the same conditions before the sample is introduced to the column.

A method called High Performance Tangential Flow Filtration (HPTFF) has been described in which a positive charge is created on the surface of an ultrafiltration membrane with a size cutoff of about 100 to about 300 kDa (van Reis et al., *J. Membr. Sci.* (2007) 297:16-et seq.; van Reis U.S. Pat. No. 7,001,550; van Reis et al., *J. Membr. Sci.* (1999) 159:133-et seq.; Bolton et al., *Adv. Filtr. Sep. Technol.* (1999) 13A:537-et seq.; Burns et al., *J. Membr. Sci.* (1999) 64:27-et seq.; Mehta et al., *CEP* (2008) 104(5):514-et seq.). When a sample of crude IgG monoclonal antibody is introduced within a narrow range of pH and conductivity, IgG is repelled from the membrane surface and thus prevented from passing through the pores. The majority of contaminant species either binds to the surface or passes through the pores by convective mass transport, and is thereby eliminated. The method also permits concentration of the antibody, although such concentration relies on antibody equilibration to the operating conditions before it is applied to the membrane. Those operating conditions generally consist of weakly alkaline to near-neutral pH and low conductivity. Excessive conductivity may block electrostatic interactions and cause IgG loss through the membrane pores. The capacity of the method may be restricted by the proportion of acidic contaminants that bind to the membrane, since they neutralize the charge on the membrane. This may weaken or suspend antibody repulsion and cause antibody to be lost by passing through the pores with contaminants. Thus, like bind-elute and flow-through applications on traditional ion exchangers, HPTFF relies on equilibration of the sample and operating conditions in advance of performing the technique. Currently, HPTFF is employed solely in membrane applications. Its fluid-recycling approach may preclude its application to monoliths or columns of packed particles.

Another method employs mixed mode chromatography media with combinations of chemical functionalities (Eriksson et al., *Bioprocess. Intl.* (2009) 7:52-et seq.; Bresolin et al., *J. Chromatogr. B* (2010) 878:2087-et seq.; de Souza et al., *J. Chromatogr. B* (2010) 878:557-et seq.). Some of these media materials include positive charges and are applied in the same format as ion exchangers, i.e. in bind-elute and flow-through mode, although under different chemical conditions depending on the nature of the secondary functionalities. Yet another method is to combine physical functionalities with chemical functionalities. One such example employs variable size exclusion functionality along with porous particle anion exchange materials (Hunter et al., *J. Chromatogr. A* (2000) 897:65-et seq.; Hunter et al., *J. Chromatogr. A* (2000) 897:87-et seq.; Hunter et al., *J. Chromatogr. A* (2001) 930:79-et seq.; Hunter et al., *J. Chromatogr. A* (2002) 971:105-et seq.). The method generally involves entry of proteins into particle pores in a size-dependent manner while also exhibiting dependence on the charge on the protein, as well as the buffer conditions. The method has been used to bind and elute an IgG-type antibody, although it has not been employed in purification or to reduce antibody aggregates.

Positively charged soluble polymers (polyallylamine, polyarginine) and certain divalent cations (ethacridine, metal ions) have been employed to co-precipitate negatively charged contaminants from antibody preparations (Thömmes et al., in: U. Gottschalk (ed.), *Process Scale Purification of Antibodies*, J. Wiley and Sons, Hoboken, (2009) 293-et seq.; Ma et al., *J. Chromatogr. B* (2010) 878:798-et seq.; Peram et al., *Biotechnol. Progr.*, (2010) 26:1322-et seq.; Glynn, in U. Gottschalk (ed.), *Process Scale Purification of Antibodies*, J. T. Wiley and Sons, Hoboken, (2009) 309-et seq.; Farhner et al., U.S. Patent Application No. 20080193981; Ma et al., *J. Chromatogr. B*

(2010) 878:798-et seq.; Cordes et al., *Biotechnol. Progr.*, (1990) 6:283-et seq.; Dissing, et al., *Bioseparation*, (1999), 7:221-et seq.; Bernhardt U.S. Pat. No. 5,559,250; Akcasu et al., *Nature*, (1960) 187:323-et seq.; Matsuzawa, et al., *Nucl. Acids Res.*, (2003) 3(3):163-et seq.; Christensen et al., *Prot. Expr. Purif.*, (2004) 37:468-et seq.; Kejnovsky et al., *Nucl. Acids Res.*, (1997) 25:1870-et seq.; Ongkudon et al., *Anal. Chem.*, (2011) 83:391-et seq.). These methods can be thought of as liquid-phase analogues to positively charged particles. Such methods can be carried out in an alternate physical format, commonly referred to as batch mode, in which the polymers are added directly to an antibody preparation within a narrow range of carefully controlled pH and conductivity conditions. Such variant methods have been employed in the selective precipitation of acidic host proteins from cell culture supernatants, as well as DNA, endotoxin, and virus.

Another issue that has been indicated is that unnatural hetero-aggregates can form spontaneously between host cell-derived contaminants and recombinant proteins produced by in vitro cell culture methods (Shukla et al., *Biotechnol. Progr.* (2008) 24:1115-et seq.; Luhrs, et al., *J. Chromatogr. B* (2009) 877:1543-et seq.; Mechetner et al., *J. Chromatogr. B* (2011) 879:2583-et seq.; Gagnon et al., *J. Chromatogr. A*, (2011) 1218:2405-et seq.; Gagnon, *Bioprocessing J.* (2010) 9(4):14-et seq.). These hetero-aggregates may be considered unnatural in two respects: 1) constituent contaminants are often of non-human origin, secreted by living non-human host cells or released into the culture media when non-human host cells lyse upon death. In living humans, such non-human contaminants do not exist; and 2) constituent contaminants accumulate to high concentrations in comparison to human in vivo systems where dead cell constituents are quickly eliminated. Accordingly, recombinant products are exposed to high levels of strongly interactive contaminants at concentrations that typically do not occur in living systems. Meanwhile, high expression levels of recombinant proteins make them suitable substrates for non-specific associations with these non-human contaminants, favoring the formation of undesirable hetero-aggregates of diverse composition.

The contaminating protein content of hetero-aggregates has been addressed to some extent via direct targeting of the contaminating protein (Shukla et al. and Gagnon et al. supra), as well as indirectly via targeting of the corresponding DNA component responsible for the contaminating protein (Luhrs et al. and Gagnon supra). A reduction of antibody aggregate level has been indicated when some complexes are dissociated (Shukla et al., Mechetner et al., and Gagnon supra). The ability of anion exchangers to reduce levels of antibody-contaminant complexes has been disclosed (Luhrs et al. and Gagnon et al. supra), but no study has revealed an anion exchange treatment that was able to fully eliminate hetero-aggregates. Size exclusion, cation exchange, and hydrophobic interaction chromatography were all generally inferior to anion exchange (Gagnon et al. supra).

Treating antibody preparations with agents that might be expected to dissociate hetero-aggregates has generally proven ineffective. For example, employing high concentrations of urea, salts, or combinations of the two does not substantially dissociate IgM-contaminant hetero-aggregates (Gagnon et al. supra). Protein A affinity chromatography with pre-elution washes of urea, alcohol, and surfactants has been indicated to reduce hetero-aggregate levels more effectively than without washes (Shukla et al. supra), as did pre-elution washes combining urea, salt, and EDTA with protein G affinity chromatography (Mechetner et al. supra). Anion exchange chromatography with a pre-elution wash of urea has been indicated to reduce hetero-aggregates more effectively than in the absence of a urea wash (Mechetner et al. supra). Cation exchange chromatography has also been indicated to reduce hetero-aggregates more effectively with a pre-elution EDTA wash than without the wash (Mechetner et al. supra). Finally, hydroxyapatite with pre-elution washes of urea and/or salt have also reduced hetero-aggregates more effectively than without such washes (Gagnon supra). Despite these observations, in general, the use of dissociating agents in pre-elution washes of antibodies bound to chromatography columns has been only moderately successful.

SUMMARY OF THE INVENTION

Methods, materials, and kits are provided for the purification of IgG-based immunological constructs. In certain embodiments, the invention provides methods for purifying a sample containing a desired protein including the steps of (i) providing a packed chromatographic column comprising positively charged porous particles, (ii) equilibrating the packed chromatographic column to the conditions to which the desired protein in the sample is to elute, (iii) contacting the sample with the packed chromatographic column such that the sample volume applied to the packed chromatographic column is less than or equal to the interparticle space of the positively charged porous particles within the packed chromatographic column, and (iv) eluting the desired protein from the packed chromatographic column, where the desired protein is in a purer state and in the conditions to which the packed chromatographic column was equilibrated; where the desired protein is an IgG antibody, IgG antibody fragment, IgG antibody derivative, or IgG antibody fusion protein.

In the preceding embodiment, the desired protein may be derived from an IgG antibody in a form selected from the group consisting of a Fab fragment, a F(ab')2 fragment, a minibody, a diabody, a VHH domain, an Fc-fusion protein, or an IgG derivative having charge properties similar to that of an IgG antibody.

In one or more of each of the preceding embodiments, the sample may be previously unpurified.

In one or more of each of the preceding embodiments, the sample may have undergone a previous purifying step to an intermediate level or high level of purity.

In one or more of each of the preceding embodiments, the intermediate level of purity of the sample may be in a range of from about 40% to about 90% purity.

In one or more of each of the preceding embodiments, the high level of purity of the sample may be in a range of from about 90% or greater.

In one or more of each of the preceding embodiments, an initial level of a host cell protein or DNA contaminant in the sample may be in a range of from about 100 ppm to about 10,000 ppm.

In one or more of each of the preceding embodiments, an initial level of total contaminant in the sample may be in a range of from about 200,000 ppm to about 5,000,000 ppm.

In one or more of each of the preceding embodiments, a final level of a contaminant in the desired protein may be in a range of from about 0.1 to about 10 ppm.

In one or more of each of the preceding embodiments, a final level of a contaminant in the desired protein may be in a range of from about 0.01 to about 1 ppm.

In one or more of the preceding embodiments, the sample volume may be less than 99% of the interparticle space of the positively charged porous particles within the column.

In one or more of the preceding embodiments, the sample volume may be less than 95% of the interparticle space of the positively charged porous particles within the column.

In one or more of each of the preceding embodiments, the sample volume may be less than 90% of the interparticle space of the positively charged porous particles within the packed chromatographic column.

In one or more of each of the preceding embodiments, the sample volume may be less than 80% of the interparticle space of the positively charged porous particles within the packed chromatographic column.

In one or more of each of the preceding embodiments, the sample volume may be less than 70% of the interparticle space of the positively charged porous particles within the packed chromatographic column.

In one or more of each of the preceding embodiments, the sample volume may be less than 10% of the interparticle space of the positively charged porous particles within the packed chromatographic column.

In one or more of each of the preceding embodiments, the sample volume may be less than 5% of the interparticle space of the positively charged porous particles within the packed chromatographic column.

In one or more of each of the preceding embodiments, the sample volume may be less than 1% of the interparticle space of the positively charged porous particles within the packed chromatographic column.

In one or more of each of the preceding embodiments, the sample volume may be less than 0.1% of the interparticle space of the positively charged porous particles within the packed chromatographic column.

In one or more of each of the preceding embodiments, the packed chromatographic column may be packed solely with positively charged porous particles and the sample volume may be less than 40% of the volume of the packed chromatographic column.

In one or more of each of the preceding embodiments, a sample application condition comprises a pH in a range of from approximately 2 to a pH of approximately 10.

In one or more of each of the preceding embodiments, the packed chromatographic column may be equilibrated to a pH between approximately 4 and approximately 9.

In one or more of each of the preceding embodiments, the packed chromatographic column may be equilibrated with a buffer at a pH between about 7.5 and about 8.5.

In one or more of each of the preceding embodiments, a sample application condition comprises a conductivity in range of from approximately 0.1 mS/cm to approximately 250 mS/cm.

In one or more of each of the preceding embodiments, the packed chromatographic column may be equilibrated to a conductivity value of from approximately 0.1 mS/cm to approximately 30 mS/cm.

In one or more of each of the preceding embodiments, the packed chromatographic column may be equilibrated to a conductivity value of from about 0.1 to about 15 mS/cm.

In one or more of each of the preceding embodiments, the packed chromatographic column may be equilibrated with a buffer at a pH of about 8 and a non-zero conductivity value less than about 1 mS/cm.

In one or more of each of the preceding embodiments, the packed chromatographic column may be equilibrated to conditions at or close to a sample application condition for a subsequent purification step to be performed upon the eluate.

In one or more of each of the preceding embodiments, the positively charged porous particles are anion exchange particles.

In one or more of each of the preceding embodiments, the anion exchange particles possess an electropositivity, at least of portion of the electropositivity being provided by a moiety selected from the group consisting of tris(2-aminoethyl)amine, polyarginine, polylysine, polyethyleneimine, polyallylamine, diethyleneaminoethyl, ethylene diamino, a primary amino moiety, a secondary amino moiety, a tertiary amino moiety, a quaternary amino moiety, a combination of electropositive species, and mixtures thereof.

In one or more of each of the preceding embodiments, the packed chromatographic column further comprises other particles in addition to the electropositive porous particles.

In one or more of each of the preceding embodiments, at least one of the electropositive porous particles or the other particles comprise one or more secondary chemical functionalities selected from the group consisting of cation exchange, hydrophobic interactions, hydrogen bonding, pi-pi interactions, and metal chelation.

In one or more of each of the preceding embodiments, the method may further comprise the additional step of contacting the sample with an aggregate-dissociating agent prior to the step of contacting the sample with the packed chromatographic column.

In one or more of each of the preceding embodiments, the aggregate-dissociating agent may be an organic cation.

In one or more of each of the preceding embodiments, the organic cation may be selected from the group consisting of ethacridine, 9-aminoacridine (aminacrine), 3,6 acridinediamine (proflavin), acrisorcin, acrizane (phenacridane), acridine orange, quinacrine, acricide, acridone, acridine-9-carboxylic acid, acranil (1-[(6-chloro-2-methoxy-9-acridinyl)amino]-3-(diethylamino)-2-propanol dihydrochloride), phenosafranin, phenoxazine, phenothiazine, acriflavine (3,6-diamino-10-methylacridinium, chloride and 3,6-acridineidiamine), arginine, and chlorhexidine.

In one or more of each of the preceding embodiments, the organic cation may be ethacridine, chlorhexidine, arginine, or a salt thereof.

In one or more of each of the preceding embodiments, the organic cation may be ethacridine or a salt thereof.

In one or more of each of the preceding embodiments, the organic cation may be present in an amount of from approximately 0.01% and approximately 0.05% (w/v).

In one or more of each of the preceding embodiments, the organic cation may be present in a non-zero amount less than approximately 0.01% (w/v).

In one or more of each of the preceding embodiments, the organic cation may be present in a non-zero amount less than approximately 0.005% (w/v).

In one or more of each of the preceding embodiments, the organic cation may be present in a non-zero amount less than approximately 0.001% (w/v).

In one or more of each of the preceding embodiments, the organic cation may be present in an amount of from approximately 0.020 and approximately 0.025% (w/v).

In one or more of each of the preceding embodiments, the sample may be treated with more than one organic cation selected from the group consisting of ethacridine, arginine, and chlorhexidine and salts thereof prior to the step of contacting the sample with the packed chromatographic column.

In one or more of each of the preceding embodiments, the organic cations used to treat the sample prior to the step of contacting the sample with the packed chromatographic column may be provided in a non-zero concentration of less than 1% (w/v).

In one or more of each of the preceding embodiments, the organic cations used to treat the sample prior to the step of contacting the sample with the packed chromatographic column may be provided in a concentration of from approximately 0.01% and approximately 0.05% (w/v).

In one or more of each of the preceding embodiments, the organic cations used to treat the sample prior to the step of contacting the sample with the packed chromatographic column may be provided in a non-zero concentration less than approximately 0.01% (w/v).

In one or more of each of the preceding embodiments, the organic cations used to treat the sample prior to the step of contacting the sample with the packed chromatographic column may be provided in a non-zero concentration less than approximately 0.005% (w/v).

In one or more of each of the preceding embodiments, the organic cations used to treat the sample prior to the step of contacting the sample with the packed chromatographic column may be provided in a non-zero concentration less than approximately 0.001% (w/v).

In one or more of each of the preceding embodiments, the organic cations used to treat the sample prior to the step of contacting the sample with the column may be provided in a concentration of from approximately 0.020 to approximately 0.025% (w/v).

In one or more of each of the preceding embodiments, the method may further comprise contacting the sample with a soluble organic modulator selected from the group consisting of nonionic organic polymers, organic solvents, surfactants, and ureides, prior to the step of contacting the sample with the packed chromatographic column.

In one or more of each of the preceding embodiments, the step of contacting the sample with the soluble organic modulator may occur prior to a step of contacting the sample with an organic cation.

In one or more of each of the preceding embodiments, the step of contacting the sample with the soluble organic modulator may occur substantially simultaneously with a step of contacting the sample with an organic cation.

In one or more of each of the preceding embodiments, the step of contacting the sample with the soluble organic modulator may occur after a step of contacting the sample with an organic cation.

In one or more of each of the preceding embodiments, the soluble organic modulator may comprise a nonionic organic polymer selected from the group consisting of polyethylene glycol, polypropylene glycol and polybutylene glycol.

In one or more of each of the preceding embodiments, the nonionic organic polymer may have a non-zero average molecular weight of approximately 500 D or less.

In one or more of each of the preceding embodiments, the soluble organic modulator may comprise an organic solvent selected from the group consisting of ethylene glycol, propylene glycol, butylene glycol, dimethylsulfoxide, ethanol, isopropanol and phenoxyethanol.

In one or more of each of the preceding embodiments, the soluble organic modulator may be provided at a concentration of approximately 1% (w/v) or greater.

In one or more of each of the preceding embodiments, the soluble organic modulator may comprise a surfactant selected from the group consisting of Tween, Triton, CHAPS, CHAPSO and octyl glucoside.

In one or more of each of the preceding embodiments, the surfactant may be provided at a non-zero concentration of approximately 1% (w/v) or less.

In one or more of each of the preceding embodiments, the surfactant may be provided at a non-zero concentration of approximately 0.1% (w/v) or less.

In one or more of each of the preceding embodiments, the soluble organic modulator may comprise a ureide provided in a subsaturating amount.

In one or more of each of the preceding embodiments, the ureide may be selected from the group consisting of urea, hydantoin, and allantoin.

In one or more of each of the preceding embodiments, the methods may further comprise contacting the sample with an antiviral agent, prior to the step of contacting the sample with the packed chromatographic column.

In one or more of each of the preceding embodiments, the antiviral agent may be an organic cation with at least one positive charge.

In one or more of each of the preceding embodiments, the antiviral agent may lack a positive charge.

In one or more of each of the preceding embodiments, the antiviral agent may be present in a non-zero amount less than approximately 1% (w/v).

In one or more of each of the preceding embodiments, the antiviral agent may be present in a non-zero amount less than approximately 0.1% (w/v).

In one or more of each of the preceding embodiments, the antiviral agent may be present in a non-zero amount less than approximately 0.01% (w/v).

In one or more of each of the preceding embodiments, the antiviral agent may be present in a non-zero amount less than approximately 0.001% (w/v).

In one or more of each of the preceding embodiments, the method may further comprise the additional steps of, prior to the step of contacting the sample with the packed chromatographic column, contacting the sample with a ureide in an amount sufficient for the ureide to be supersaturated in the sample, and separating the supernatant comprising the desired protein from the solid or undissolved portions of the sample.

In one or more of each of the preceding embodiments, the step of contacting the sample with the ureide may occur prior to a step of contacting the sample with an organic cation.

In one or more of each of the preceding embodiments, the step of contacting the sample with the ureide may occur substantially simultaneously with a step of contacting the sample with an organic cation.

In one or more of each of the preceding embodiments, the step of contacting the sample with the supersaturated ureide occurs after a step of contacting the sample with a soluble organic cation of mixed chemical character.

In one or more of each of the preceding embodiments, the ureide may be selected from the group consisting of urea, uric acid, hydantoin, allantoin, alcloxa, aldioxa, hemocane, ureidohydantoin, 5-ureidohydantoin, glyoxylureide, glyoxylic acid diureide, 2,5-dioxo-4-imidazolidinyl urea, and purines.

In one or more of each of the preceding embodiments, the ureide may comprise allantoin.

In one or more of each of the preceding embodiments, the ureide may comprise uric acid.

In one or more of each of the preceding embodiments, the allantoin may be present in an amount greater than 0.5% (w/v).

In one or more of each of the preceding embodiments, the allantoin may be present in an amount greater than approximately 1% (w/v).

In one or more of each of the preceding embodiments, the uric acid may be present in an amount greater than 0.0025% (w/v).

In one or more of each of the preceding embodiments, the uric acid may be present in an amount greater than approximately 0.01% (w/v).

In one or more of each of the preceding embodiments, the uric acid may be present in an amount greater than approximately 0.1% (w/v).

In one or more of each of the preceding embodiments, the uric acid may be present in an amount greater than approximately 1% (w/v).

In one or more of each of the preceding embodiments, the method may further comprise the additional step of removing insoluble solids prior to the step of contacting the sample with the packed chromatographic column.

In one or more of each of the preceding embodiments, the step of removing insoluble solids may be performed after contacting the sample with one or more of an organic modulator, an antiviral agent or a supersaturated ureide.

In one or more of each of the preceding embodiments, after contacting the sample with one or more of an organic modulator, an antiviral agent or a supersaturated ureide, the sample may be contacted with a solid material having chemical moieties capable of adsorbing at least some of the organic modulator, the antiviral agent and the ureide added to the sample.

In one or more of each of the preceding embodiments, the solid material may be composed of particles added to the sample and subsequently separated from the sample.

In one or more of each of the preceding embodiments, the solid material may be composed of a membrane, a monolith, or column packed with particles through or across which the sample may be passed.

In one or more of each of the preceding embodiments, the chemical moieties on the solid materials may comprise one or more of groups having the capacity for cation exchange, anion exchange, hydrophobic interactions, hydrogen bonding, pi-pi interactions, or metal chelation.

In one or more of each of the preceding embodiments, the method may further comprise the additional step of separating from or removing insoluble solids from the sample after the step of contacting the sample with the solid material having chemical moieties capable of adsorbing at least some of the organic modulators, antiviral agents and ureides added to the sample and prior to the step of contacting the sample with the packed chromatographic column.

In one or more of each of the preceding embodiments, the sample may contain aggregates, wherein a purer state of the desired protein has a reduced aggregate content in comparison with the sample.

In one or more of each of the preceding embodiments, the aggregates may comprise homo-aggregates of the desired protein.

In one or more of each of the preceding embodiments, the presence of homo-aggregates of the desired protein in the sample may be substantially eliminated by performing the methods disclosed herein.

In one or more of each of the preceding embodiments, the aggregates may comprise hetero-aggregates of the desired protein and a contaminant.

In one or more of each of the preceding embodiments, the hetero-aggregates may be of substantially the same hydrodynamic size as the desired protein.

In one or more of each of the preceding embodiments, the contaminant may be a nucleic acid, nucleotide, endotoxin, metal ion, protein, lipid, cell culture media component, or combinations thereof.

In one or more of each of the preceding embodiments, the presence of hetero-aggregates of the desired protein and the contaminant may be substantially eliminated by performing the methods disclosed herein.

In one or more of each of the preceding embodiments, the sample may contain one or more contaminants wherein the purer state of the desired protein has a reduced content of such contaminants in comparison with the sample as a result of performing the methods disclosed herein.

A kit may be provided for the convenient practice of a method according to any of the preceding embodiments.

Although embodiments disclosed herein may be exemplified primarily with reference to IgG type antibodies and their hetero-aggregates, those skilled in the art will appreciate the applicability of various embodiments to the purification of other proteins, such as IgM-type and other antibodies, histone proteins, and beneficially, any other alkaline proteins. These and other advantages will be recognized by those skilled in the art.

DETAILED DESCRIPTION OF THE INVENTION

Figure 1:
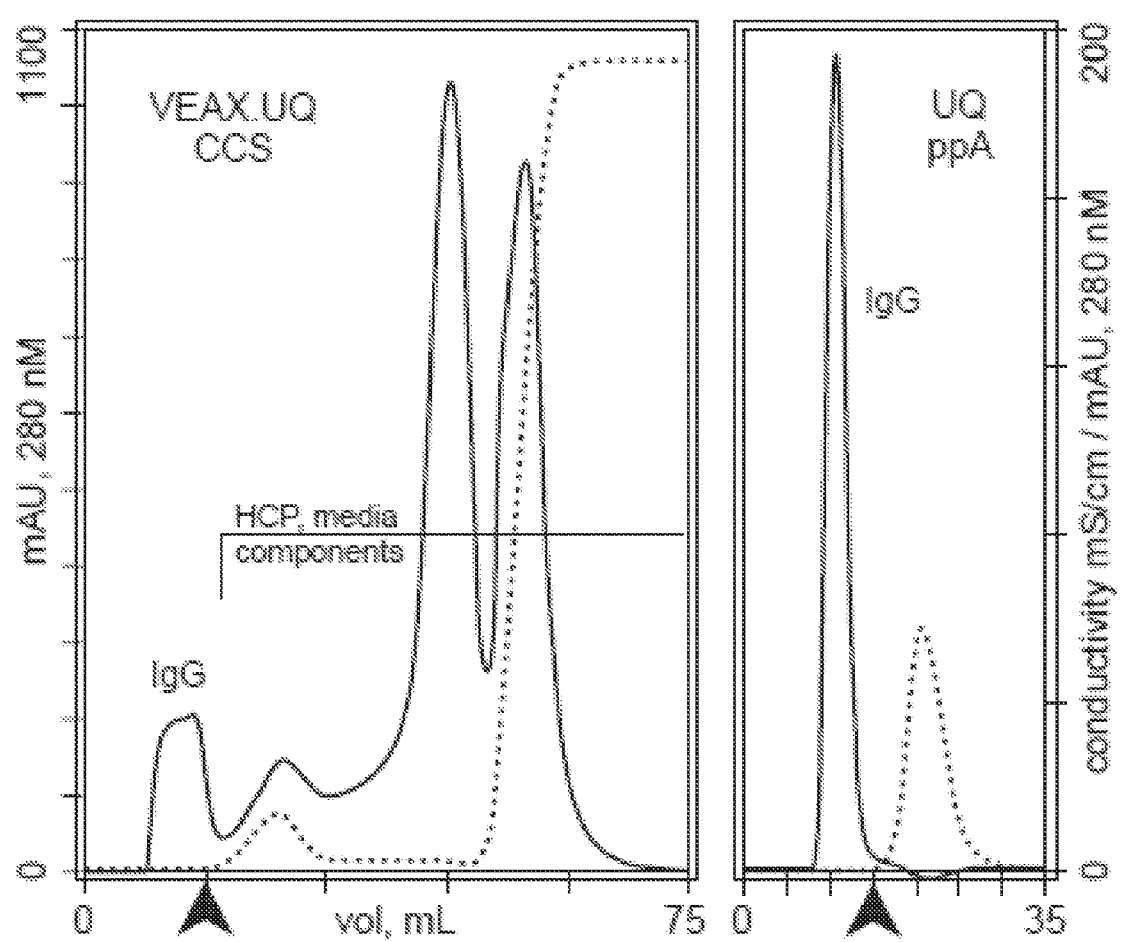
FIG. 1 shows side-by-side chromatograms of filtered cell culture supernatant (CCS) (left panel) and protein A-purified trastuzumab (right panel) applied to UNOsphere Q at sample volume 35% of column volume with both columns equilibrated to 50 mM Tris, pH 8.0. The solid line indicates UV absorbance. The broken line indicates conductivity.

In certain embodiments, the present invention relates to a column packed with electropositive porous particles in which an antibody may be substantially restricted to the space between particles (i.e. the inter-particle or void space) by the force of electrostatic repulsion, independently from or in combination with steric rejection from the pores, or solely by steric rejection from the pores. This may cause the antibody to transit the column substantially if not exclusively through the void space. Steric rejection, in particular, refers to a mechanism whereby antibody molecules are unable to enter the pore space under conditions which prevent them from overcoming physical resistance exerted by the configuration of positively charged ligands within the pores. Many of the contaminating proteins (including those arising from the host cell from which the antibody was produced), DNA fragments, and cell culture media components, including salts, nonionic, and zwitterionic species are able to enter the pores of the particles, which is believed, without being bound to any specific theory, to retard their transport through the column and causes them to become separated from the faster-migrating IgG as buffer flows through the column. Acidic contaminants including DNA, endotoxin, virus, and many proteins may be further retarded by binding to the electropositive surface. It has been discovered that this method permits effective fractionation of, inter alia, IgG without respect to the sample conditions, without respect to the chemical characteristics of most contaminants, and without respect to the composition of the buffer that is applied immediately following sample application to impel the antibody through the column. In certain embodiments, it is an advantage of the invention that it may be practiced at a wide range of conditions (pH, salt concentration, conductivity, etc.) and therefore those conditions may be selected for convenient performance of the methods of the invention in conjunction with processes preceding or following the methods of the invention in the course of the manufacture and purification of a desired IgG antibody or fragment. In certain embodiments, these unique operating features and results are achieved by limiting sample application to a volume not exceeding the inter-particle volume of the positively charged particles within the column. Additionally, in some embodiments, the method is neither applied with other types of positively charged materials, including non-porous particles, membranes, or monoliths, nor is it applied by dispersing positively charged porous or non-porous particles or soluble positively charged polymers within a sample. Rather, in preferred embodiments of the invention, the method is performed with a packed column of porous particles.

It has been further discovered that in certain embodiments, the innate fractionation ability of certain methods of the invention may be enhanced by including additional surface functionalities on particles within the column bed, so long as the column is equilibrated to conditions that do not cause the antibody to be retained or significantly retarded by those additional functionalities. Such functionalities may include but are not restricted to negatively charged groups, hydrophobic groups, pi-pi bonding groups, hydrogen-bonding groups, or metal-chelation groups. These additional functionalities may reside on the same chemical structure as the positively charged groups, on the same porous particles as the positively charged groups, or on different particles that may be porous or non-porous. In the event that secondary functionalities are added through inclusion of additional particles, the volume of sample that may be applied is limited to a volume corresponding to the inter-particle space that would exist between only the positively charged porous particles in the column. This volume can be estimated at about 40% of the gravity-settled volume of positively charged porous particles in a column, but may be less if the particle bed is physically compressed, and can be determined quantitatively by experimentation.

In certain embodiments, the invention provides the advantage that the method permits the substantial reduction of the proportion of antibody aggregates in a sample. This is surprising because aggregates are expected to have the same charge properties as native antibodies. Aggregates are therefore expected to co-elute with native antibodies. Without being bound to any specific theory, it is believed that in certain embodiments, the method of the invention dissociates aggregates rather than removing them.

In certain embodiments, aggregate reduction can be further enhanced by pre-treating the sample with agents to promote dissociation of aggregates. Such agents particularly include multivalent cations such as ethacridine, and may further include various organic modulators including elevated concentrations of salts, ureides, amino acids, nonionic organic polymers, organic solvents, and surfactants, among others. The dissociating agents are removed with other small molecules in the sample, during routine practice of the method. Experimental data indicate that the combination of sample pre-treatment with positively charged aggregate-dissociating agents, followed by application of the sample to the column as described above, achieves a greater degree of aggregate reduction than either method alone. Other organic or inorganic compounds may be added for other purposes, such as but not limited to virus inactivation, including but not limited to antiviral agents such as benzalkonium chloride, methylene blue, and tri(n-butyl) phosphate.

In certain embodiments, the invention provides methods for purifying a sample containing a desired protein including the steps of (i) providing a packed chromatographic column comprising positively charged porous particles, (ii) equilibrating the column to the conditions to which the desired protein in the sample is to elute, (iii) contacting the sample with the column such that the sample volume applied to the column is less than or equal to the interparticle space of the positively charged porous particles within the column, (iv) eluting the desired protein from the column, where the desired protein is in a purer state and in the conditions to which the column was equilibrated; where the desired protein is an IgG antibody, IgG antibody fragment, IgG antibody derivative, or IgG antibody fusion protein.

In certain embodiments, the desired protein is an IgG antibody or is derived from an IgG antibody in a form such as a Fab fragment, a F(ab')$_2$ fragment, a minibody, a diabody, a VHH domain, an Fc-fusion protein, or an IgG derivative having charge properties similar to that of an IgG antibody. In certain embodiments, the sample may be unpurified, at an intermediate level of purity, or highly purified.

In other embodiments, the antibody may be an IgM, IgD, IgA, or IgE, or derivative forms of those antibodies, such as an Fab fragment, an F(ab')2 fragment, an ScFV; or a compound construct such as an Fc-fusion protein or an immunoconjugate.

In certain embodiments, the inter-particle space is greater than approximately twice the volume of the sample. In certain embodiments, the inter-particle space of the portion of the column containing porous electropositive particles is greater than the sample volume. In certain embodiments, having columns packed solely with positively charged porous particles the sample volume is about 40% or less than the volume of the packed column; in certain embodiments having columns packed with positively charged porous particles and other particles, the sample volume is about 40% or less than the volume of the gravity settled positively charged porous particles in the column.

In certain embodiments, the interparticle space of the positively charge porous particles packed in the columns is approximately the same volume as the sample, or 10% greater than the sample volume, or 20, 30, 40, 50, 60, 70, 80, 90, or 100% greater than the sample, or 1.5 or 2 or 2.5 or 3 or 4 or 5 or more times greater than the sample.

In certain embodiments, the column is equilibrated with an equilibration buffer prior to contacting the sample with the column. In certain such embodiments, the column is equilibrated to a pH between approximately 4 and approximately 9. In certain such embodiments, the column is equilibrated with a buffer at a pH between about 6.5 and about 7.5. In certain embodiments, the column is equilibrated to a conductivity value of from approximately 1 mS/cm and approximately 30 mS/cm. In certain embodiments, the pH, salt concentration and conductivity conditions for the column are selected such that electrostatic interactions between the electropositive porous particles and components from the sample other than the desired protein are substantially suspended. The pH, salt concentration and conductivity conditions for the equilibration buffer and or the elution buffer may be chosen in certain embodiments of the invention such that electrostatic interactions between the electropositive porous particles and components from the sample other than the desired protein are substantially suspended. In certain embodiments, the conductivity of the equilibrated column is between about 0.1 and about 15 mS/cm. In certain embodiments, the column may be equilibrated to conditions at or close to the sample application conditions for a subsequent purification step to be performed upon the eluate.

In certain embodiments, the sample conditions may range from pH of approximately 2 to a pH of approximately 10. In certain such embodiments, the conductivity values of the sample may range from approximately 0.1 mS/cm to approximately 250 mS/cm. In certain embodiments, the sample conditions may range from pH of approximately 2 to a pH of approximately 10 and in certain embodiments, the conductivity values of the sample conditions may range from approximately 0.1 mS/cm to approximately 250 mS/cm.

In certain embodiments, the elution conditions may range from a pH of approximately 2 to a pH of approximately 10. In certain such embodiments, the conductivity of the buffer applied immediately after the sample may range from approximately 0.1 mS/cm to approximately 250 mS/cm. In certain embodiments, the buffer applied immediately after the sample has lower conductivity than the sample or equilibration buffer. In certain embodiments, the buffer applied immediately after the sample has higher conductivity than the sample or equilibration buffer.

In certain embodiments, the column equilibration buffer may be of a pH of about 8.0 and a conductivity of less than 1 mS/cm, such as mediated by a 50 mM or lower concentration of Tris without added salt. In some embodiments, the concentration of Tris may be in a range of from about 20 mM to about 50 mM.

In certain embodiments, the buffer applied immediately after the sample may have the same composition as the equilibration buffer. In certain embodiments, the buffer applied after the sample may have a different composition from the equilibration buffer. In certain embodiments, the buffer applied immediately after the sample may be of much higher conductivity than the equilibration buffer, with the object of removing negatively charged materials that may be bound to the positively charged particles.

In certain embodiments, excess salt or other additives may be included in the sample to clean the column in preparation for a subsequent usage cycle. It will be understood that such additives may also mediate the beneficial effect of dissociating non-specific interactions between the antibody and contaminant species, with the result of increasing the degree of purity and or aggregate reduction achieved by the technique.

In certain embodiments, the positively charged porous particles are anion exchange particles. In certain such embodiments, the anion exchange particles possess an electropositivity which is conferred in part by a moiety such as a primary amino group, a secondary amino group, a tertiary amino group, a quaternary amino group, ethylene diamino, diethyaminoethyl, tertiary amino ethyl, quaternary amino ethyl, tris(2-aminoethyl)amine, polyallylamine, polyarginine, polylysine, or polyethyleneimine. In certain embodiments, the column contains particles in addition to the electropositive porous particles. In certain embodiments, at least one of the electropositive porous particles and the additional particles possess one or more secondary chemical functionalities selected from the group consisting of cation exchange, hydrophobic interactions, hydrogen bonding, pi-pi interactions, and metal chelation.

In certain embodiments, the technique makes use of so-called grafted-ligands that create a dense network of charged groups within the pores of the particles, such that the network physically hinders or prevents the entry of proteins that lack a strong negative charge.

In certain embodiments, the technique makes use of positively charged porous particle chromatography media having a pore size that prevents effective entry of IgG or fragments thereof. Exemplary pore sizes useful in preventing entry of IgG or fragments thereof include a range of from about 10 nm to about 100 nm, including any values in between and fractions thereof, depending on the size of the IgG or fragment thereof. One skilled in the art will appreciate that pore sizes less than 10 nm may also be employed including, without limitation, 1, 2, 3, 4, 5, 6, 7, 8, or 9 nm. Likewise, one skilled in the art will also appreciate that pore sizes greater than 100 nm may be employed including, without limitation, 120, 150, 200, 300, and 500 nm, including any values in between and fractions thereof. Those skilled in the art will recognize an appropriate selection of pore size based on the antibody or fragment thereof to be purified. Such porous particles may constitute the entire sample volume, or any smaller proportion thereof.

In certain embodiments, the invention provides for the additional step of contacting the sample with an aggregate-dissociating agent prior to the step of contacting the sample with the column. In certain such embodiments, the aggregate-dissociating agent is an organic cation. In certain embodiments, such organic cations may be ethacridine, 9-aminoacridine (aminacrine), 3,6 acridinediamine (proflavin), acrisorcin, acrizane (phenacridane), acridine orange, quinacrine, acricide, acridone, acridine-9-carboxylic acid, acranil (1-[(6-chloro-2-methoxy-9-acridinyl)amino]-3-(diethylamino)-2-propanol dihydrochloride), phenosafranin, phenoxazine, phenothiazine, acriflavine (3,6-diamino-10-methylacridinium, chloride and 3,6-acridineidiamine), or chlorhexidine. In certain embodiments, the organic cation of is arginine, ethacridine,—or chlorhexidine or a salt thereof. In certain aspects of the invention, the organic cation is ethacridine or a salt thereof. In certain such embodiments, the organic cation is present in an amount of from approximately 0.01% to approximately 0.05%, or in a non-zero amount less than approximately 0.01%, or in a non-zero amount less than approximately 0.005%, or in a non-zero amount less than approximately 0.001%, or in an amount of from approximately 0.020 to approximately 0.025%.

In certain embodiments, the sample is treated with more than one organic cation from the group consisting of arginine, ethacridine, and chlorhexidine and salts thereof prior to the step of contacting the sample with the column. In certain such embodiments, the organic cations used to treat the sample prior to the step of contacting the sample with the column are provided in a non-zero concentration of less than 1%, or in a concentration of from approximately 0.01% to approximately 0.05%, or in a non-zero concentration less than approximately 0.01%, or in a non-zero concentration less than approximately 0.005%, or in a non-zero concentration less than approximately 0.001%, or in a concentration of from approximately 0.020 to approximately 0.025%.

In certain embodiments, the sample is additionally contacted with a soluble organic modulator selected from the group consisting of nonionic organic polymers, organic solvents, surfactants, and ureides, prior to the step of contacting the sample with the column. In certain such embodiments, the step of contacting the sample with the organic modulator occurs prior to the step of contacting the sample with the organic cation. In others, the step of contacting the sample with the organic modulator occurs substantially simultaneously with the step of contacting the sample with the organic cation. In others, the step of contacting the sample with the organic modulator occurs after the step of contacting the sample with the organic cation. In certain such embodiments, the organic modulator is a nonionic organic polymer selected from the group consisting of polyethylene glycol, polypropylene glycol and polybutylene glycol. In certain such embodiments, the nonionic organic polymer has an average molecular weight of approximately 500 D or less. In certain such embodiments, the organic modulator is an organic solvent selected from the group consisting of ethylene glycol, propylene glycol, butylene glycol, dimethylsulfoxide, ethanol, and phenoxyethanol. In certain such embodiments, the organic modulator is provided at a concentration of approximately 1% (w/v) or greater.

In certain embodiments, the organic modulator is a surfactant selected from the group consisting of Tween, triton, CHAPS, CHAPSO and octyl glucoside. In certain such embodiments, the surfactant is provided at a non-zero concentration of approximately 1% (w/v) or less, or at a non-zero concentration of approximately 0.1% (w/v) or less. In certain embodiments, the organic modulator is a ureide provided in a subsaturating amount. In certain such embodiments, the ureide is urea, hydantoin, or allantoin.

In certain embodiments, the sample is additionally contacted with an antiviral agent, prior to the step of contacting the sample with the column. In certain such embodiments, the antiviral agent is a non-multivalent organic cation such as benzalkonium chloride, methylene blue, tri (n-butyl) phosphate, or octanoic acid (also known as caprylic acid). In certain such embodiments, the antiviral agent is present in a non-zero amount less than approximately 1% (w/v), or in a non-zero amount less than approximately 0.1% (w/v), or in a non-zero amount less than approximately 0.01% (w/v), or in a non-zero amount less than approximately 0.001% (w/v).

In certain embodiments, invention includes the additional steps of, prior to the step of contacting the sample with the column, contacting the sample with a ureide in an amount sufficient for the ureide to be supersaturated in the sample, and separating the supernatant containing the desired protein from the solid or undissolved portions of the sample. In certain such embodiments, the step of contacting the sample with the ureide occurs prior to the step of contacting the sample with the organic cation. In others, the step of contacting the sample with the ureide occurs substantially simultaneously with the step of contacting the sample with the organic cation. In yet others, the step of contacting the sample with the ureide occurs after the step of contacting the sample with the soluble organic cation of mixed chemical character. In certain such embodiments, the ureide is a urea, uric acid, hydantoin, allantoin, alcloxa, aldioxa, hemocane, ureidohydantoin, 5-ureidohydantoin, glyoxylureide, glyoxylic acid diureide, 2,5-dioxo-4-imidazolidinyl urea, or a purine. In certain such embodiments, the ureide is allantoin or uric acid. In certain embodiments where the ureide is allantoin, the allantoin is present in an amount greater than 0.5% (w/v), or in an amount greater than approximately 1% (w/v). In certain embodiments where the ureide is uric acid, the uric acid is present in an amount greater than 0.0025% (w/v), or in an amount greater than approximately 0.01% (w/v), or in an amount greater than approximately 0.1% (w/v), or in an amount greater than approximately 1% (w/v), or in an amount greater than approximately 10% (w/v).

In certain embodiments, the invention provides methods including the additional step of removing insoluble solids prior to the step of contacting the sample with the column. In certain such embodiments, the step of removing insoluble solids is performed after the step or steps of one or more of contacting the sample with an organic modulator, antiviral agent or supersaturated ureide. In certain embodiments, after the step or steps of one or more of contacting the sample with an organic modulator, antiviral agent or supersaturated ureide, the sample is contacted with a solid material having chemical moieties capable of adsorbing at least some of the organic modulators, antiviral agents and ureides added to the sample. In certain such embodiments, the solid material is composed of particles added to the sample and subsequently separated from the sample or the solid material is composed of a membrane, a monolith, or column packed with particles through or across which the sample is passed. In certain such embodiments, the chemical moieties on the solid materials may include one or more of groups having the capacity for cation exchange, anion exchange, hydrophobic interactions, hydrogen bonding, pi-pi interactions, or metal chelation. In certain embodiments, the invention provides methods including the additional step of separating from or removing insoluble solids from the sample after the step of contacting the sample with the solid material having chemical moieties capable of adsorbing at least some of the organic modulators, antiviral agents and ureides added to the sample and prior to the step of contacting the sample with the column.

In certain embodiments, the sample contains aggregates wherein the purer state of the desired protein resulting from performance of the method has a reduced aggregate content in comparison with the sample. In certain such embodiments, the aggregates comprise homo-aggregates of the desired protein and in certain of such embodiments, the presence of homo-aggregates of the desired protein in the sample is substantially eliminated. In certain embodiments, the aggregates comprise hetero-aggregates of the desired protein and a contaminant and in certain of such embodiments, the hetero-aggregates are of substantially the same hydrodynamic size as the desired protein. In certain such embodiments, the contaminant is a nucleic acid, nucleotide, endotoxin, metal ion, protein, lipid, or cell culture media component. In certain such embodiments, the presence of hetero-aggregates of the desired protein and a contaminant is substantially eliminated.

In certain embodiments, the invention provides methods in which the sample contains one or more contaminants wherein the purer state of the desired protein resulting from performance of the method has a reduced content of such contaminants in comparison with the sample. For example, in some embodiments, where the contaminant is an aggregate, the aggregate concentration may be reduced from about 20% to about 0.1%, as demonstrated in Examples 1-10 below. In some embodiments, some contaminants, such as free light chain contaminants can be nominally eliminated at the limits of detection as shown in exemplary Examples 13 and 14. Similarly, a reduction of 99% of host cell protein, DNA, endotoxin, and virus can be eliminated by way of methods of the invention as indicated, for example, in Examples 20 and 21. Methods of the present invention also compare favorably to conventional methods of purification known in the art. For example, as indicated in Example 23, a host cell protein concentration of 123 ppm could be achieved in Herceptin purification by protein A. By contrast, methods of the invention were able to reduce host cell content to about 3 ppm.

In certain embodiments, the invention provides a kit for the convenient practice of a method of the invention including some or all of the materials needed for performance of the invention, preferably in amounts and concentrations convenient for the performance of a method of the invention. Such kits may also include instructions for use of the materials provided in the kit.

The following terms are defined so that the invention may be understood more readily. Additional definitions are set forth throughout the detailed description.

"Aggregate(s)" refers to an association of two or more molecules that is stable at physiological conditions and may remain stable over a wide range of pH and conductivity conditions. Aggregates frequently comprise at least one biomolecule such as a protein, nucleic acid, or lipid and another molecule or metal ion. The association may occur through any type or any combination of chemical interactions. Aggregates of antibodies can be classified into two categories: "Homo-aggregates" refers to a stable association of two or more antibody molecules; "Hetero-aggregates" refers to a stable association of one or more antibody molecules with one or more non-antibody molecules. The non-antibody component may consist of one more entities from the group consisting of a nucleotide, an endotoxin, a metal ion, a protein, a lipid, or a cell culture media component.

"Antibody" refers to an immunoglobulin, composite, or fragmentary form thereof. The term may include but is not limited to polyclonal or monoclonal antibodies of the classes IgA, IgD, IgE, IgG, and IgM, derived from human or other mammalian cell lines, including natural or genetically modified forms, collectively "antibody derivatives," such as humanized, human, single-chain, chimeric, synthetic, recombinant, hybrid, mutated, grafted, and in vitro generated antibodies. "Antibody" may also include composite forms including but not limited to fusion proteins containing an immunoglobulin moiety. Exemplary antibody fusion proteins include, without limitation, antibodies fused with other antibodies, antibodies fused with other proteins having binding specificity for other targets, or fusion with other proteins with therapeutic, imaging, or diagnostic value. "Antibody" may also include antibody fragments such as Fab, F(ab')$_2$, Fv, scFv, Fd, dAb, Fc and other compositions, whether or not they retain antigen-binding function.

"IgG antibody," in particular, refers to an immunoglobulin, composite, fragmentary or derivative form thereof. The term may include but is not limited to polyclonal or monoclonal antibodies of any subclass derived from human or other mammalian cell lines, including natural or genetically modified forms such as humanized, human, single-chain, chimeric, synthetic, recombinant, hybrid, mutated, grafted, and in vitro generated antibodies. It may also include antibody fragments such as Fab, F(ab')$_2$, Fv, scFv, Fd, dAb, Fc, VHH, minibodies, diabodies, and other compositions, whether or not they retain antigen-binding function. It may also include composite forms including but not limited to fusion proteins containing an immunoglobulin moiety.

"Column equilibration" refers to achieving a stable and equal distribution of a desired buffer in a column packed with a chromatography medium. At equilibrium, the pH, conductivity and UV absorption of eluent measured at a column outlet, are substantially identical to the eluent being introduced at the column inlet.

"Column volume" refers to the total volume of packed particles within a usually cylindrical device called a column. The term column volume is generally understood to correspond to the so-called total column volume, which is comprised of three parts, those being the interparticle space known as the void volume, the volume within the pores known as the pore volume, and the volume occupied by the solid matrix of the particle frequently referred to as the matrix volume.

"Conductivity value" refers to ability of an electrolyte solution to conduct electricity. The conductivity of a solution of an electrolyte can be measured by, for example, determining the resistance of the solution between two electrodes separated by a fixed distance.

"Contaminant" refers to any undesired inorganic or organic entity that reduces the purity of a desired protein, such as a desired antibody. Contaminants include entities that can form aggregates with the desired protein, especially hetero-aggregates. Methods of the invention can provide for the active dissociation of such aggregates to recover the desired protein from the contaminant that forms the aggregate. Exemplary contaminants include proteins, DNA, cell components, and the like. Other contaminants may include reagents employed in prior purification steps.

"Electropositive porous particle" or "positively charged porous particle" refers to an insoluble solid that may be roughly spherical or not, and may have pores of any size. Optionally particles may be of a size ranging from less than 10 to more than 100 microns and the average pore size may range from less than 10 nm (microporous) to more than 100 nm (macroporous). Electropositivity of a particle may be conferred by chemical groups including but not limited to weak anion exchange groups, like amino, ethylene diamino, diethylaminoethyl, polyallylamine, polyethyleneimine, strong anion exchange groups, such as quaternary amino groups, combined weak-strong exchangers, such as polylysine, polyarginine, or Tris(2-aminoethyl)amine, diethylenetriamine, triethylenetetramine, tetraethylenepentamine, polypropyleneimine tetraamine, PAMAM dendrimer (ethylenediamine core), or any combinations of the foregoing. Secondary functionalities that create a mixed chemical character on a positively charged surface may consist of negatively or positively charged groups, hydrophobic groups, pi-pi bonding groups, hydrogen-bonding groups, or metal-chelation groups. The secondary functionalities may exist on electropositive particles as an inadvertent byproduct of the manufacturing materials or process by which the particles are synthesized, or they may be present by deliberate design. The concentration of secondary functionalities may range from less than 1milliequivalent per mL of particles, to more than 100 milliequivalents per mL. The term electropositive porous particle includes commercial porous particle chromatography materials referred to as anion exchangers and salt-tolerant anion exchangers, and may include so-called mixed mode chromatography materials that are electropositive.

"Endotoxin" refers to a toxic heat-stable lipopolysaccharide substance present in the outer membrane of gram-negative bacteria that is released from the cell upon lysis. Endotoxins can be generally acidic due to their high content of phosphate and carboxyl residues, and can be highly hydrophobic due to the fatty acid content of the lipid-A region. Endotoxins can offer extensive opportunity for hydrogen bonding.

"Inter-particle volume" or "void volume" refers to the volume within a column not occupied by the particles themselves; the space between the particles. This is frequently referred to as the void volume of a column. For roughly spherical particles of similar size, the void volume typically constitutes about 40% of a column packed with those particles when the particles are settled by gravity and not physically compressed by mechanical means.

"Pore volume" refers to the volume within the pores of porous particles. The pores maybe physically unobstructed, with positively charged groups distributed primarily on the pore walls, or partially obstructed with positively charged groups distributed on or within a network of polymers residing within the pores. Where the pores are partially obstructed, the degree of apparent obstruction may vary with the charge characteristics of the antibody or other sample components, and/or as a function of buffer conditions such as pH and conductivity.

"Non-ionic organic polymer" refers to a naturally occurring or synthetic hydrocarbon composed of linked repeating organic subunits that lack charged groups. It may be linear, dominantly linear with some branching, or dominantly branched. Examples suitable to practice the invention include but are not limited to polyethylene glycol (PEG), polypropylene glycol, and polyvinylpyrrolidone (PVP). PEG has a structural formula HO—$(CH_2—CH_2—O)_n$—H. Examples include, but are not limited to compositions with an average polymer molecular weight ranging from less than 100 to more than 1000 daltons.

"Organic cation" refers to an organic molecule, cation or salt of natural or synthetic origin that bears at least one positive charges and may contain multiple positive charges. The organic cation may also bear negative charges such that it has a net positive or net neutral charge. Where the organic cation is net positive it may be provided together with anions such as chlorides, bromides, sulfates, organic acids, lactates, gluconates, and any other anion not incompatible with the method. In certain embodiments certain of the positive charges of the organic cation are supplied by amine, imide or other nitrogen moieties. The organic cation may additionally be of mixed chemical character and include hydrophobic residues, other functional moieties and/or it may possess the ability to participate in other types of chemical interactions including, for example, the ability to participate in hydrogen bonds, hydrophobic interactions, pi-pi bonding, metal coordination, and intercalation. Examples of organic cations in certain embodiments include but are not limited to amino acids, diamino acids, chlorhexidine, and ethacridine. Variants and derivatives of ethacridine are understood to include 9-aminoacridine (aminacrine), 3,6 acridinediamine (proflavin), acrisorcin, acrizane (phenacridane), acridine orange, quinacrine, acricide, acridone, acridine-9-carboxylic acid, acranil (1-[(6-chloro-2-methoxy-9-acridinyl)amino]-3-(diethylamino)-2-propanol dihydrochloride), phenosafranin, phenoxazine, phenothiazine, acriflavine (3,6-diamino-10-methylacridinium, chloride and 3,6-acridineidiamine), and salts thereof (e.g. chlorides, bromides, sulfates, lactates, gluconates.) Organic cations may include other chemical groups and functionalities so long as the dominant electrostatic functionality is positive.

"Organic modulator" refers to an organic compound that can reduce or, in conjunction with other reagents, aid in reducing aggregate contamination by promoting the dissociation of aggregates of a desired protein to be purified. Organic modulators can include, without limitation, salts, ureides, amino acids, nonionic organic polymers, organic solvents, and surfactants, among others.

"Organic solvent" refers to naturally occurring or synthetic organic compound existing in a liquid state. Examples suitable to practice the invention include but are not limited to ethylene glycol, propylene glycol, dimethyl sulfoxide, ethanol, and phenoxyethanol.

"Polynucleotide" refers to a biopolymer composed of multiple nucleotide monomers covalently bonded in a chain. DNA (deoxyribonucleic acid) and RNA (ribonucleic acid) are examples of polynucleotides. Polynucleotides can have a high propensity for formation of hydrogen bonds.

"Protein" refers to any of a group of complex organic macromolecules that contain carbon, hydrogen, oxygen, nitrogen, and usually sulfur and are composed principally of one or more chains of amino acids linked by peptide bounds. The protein may be of natural or recombinant origin. Proteins may be modified with non-amino acid moieties such as through glycosylation, pegylation, or conjugation with other chemical moieties. Examples of proteins include but are not limited to antibodies, clotting factors, enzymes, and peptide hormones.

"Protein preparation" refers to any aqueous or mostly aqueous solution containing a protein of interest, such as a cell-containing cell culture harvest, a (substantially) cell-free cell culture supernatant, or a solution containing the protein of interest from a stage of purification.

"Sample application condition" refers to how the sample containing the desired protein is supplied and includes, for example, sample concentration, eluent conductivity, and the like. The sample application condition may generally be selected to the conditions under which the column is equilibrated for the ensuing purification.

"Solid material" refers to an insoluble organic solid that may be particulate, crystalline, polymeric, fibrous, porous-hollow fibrous, monolithic, or membranaceous in nature. It may consist of non-porous or porous particles, a porous membrane, a porous filter, or a porous monolith. If particulate, the particles may be roughly spherical or not, and may be of sizes ranging from less than 100 nm to more than 100 microns. The average pore size of porous particles may range from less than about 10 nm (microporous) to more than about 100 nm (macroporous). The average pore size in membranes may range from less than 100 nm to more than 1 micron. The average channel size in membranes or monoliths may range from less than 1 micron to more than 10 microns. The solid material may further consist of compound constructions, for example in which particles are embedded in a reticular matrix, sandwiched between membranes, or both.

"Supersaturated ureide" refers to a solution containing an amount of ureide in excess of its maximum solubility under the conditions prevailing in a particular protein preparation. In certain embodiments, the invention provides a sample with a ureide present in an amount greater than such ureide's solubility in such sample under the conditions for such sample such that some fraction of such ureides is present in an undissolved form in the sample.

"Surfactant" includes "surface active agents" such as a class of organic molecules that generally embody a hydrophobic portion and a hydrophilic portion, causing them to be referred to as amphiphilic. At sufficient concentrations in aqueous solutions, surfactants can self-associate into clusters with the hydrophobic portions concentrated at the center to minimize contact with water, and the hydrophilic portions radiating outwards to maximize contract with water. In the presence of biological preparations, especially those containing materials that have a hydrophobic character or possess areas of hydrophobic character, the hydrophobic portion of surfactants tend to associate spontaneously with some portions of the hydrophobic material and increase their solubility through the influence of the hydrophilic portion of the surfactant. They may also be used to modulate hydrophobic interactions that occur between differing hydrophobic materials both dissolved in an aqueous solvent. Examples of surfactants suitable for practicing certain embodiments of the invention include but are not limited to nonionic surfactants such as polysorbate surfactants (e.g., Tween 20, Polyoxyethylene (20) sorbitan monolaurate, and Tween 80, Polyoxyethylene (20) sorbitan monooleate) and Triton (e.g., polyethylene glycol p-(1,1,3,3-tetramethylbutyl)-phenyl ether), and zwitterionic surfactants such as CHAPS (3-[(3-Cholamidopropyl)dimethylammonio]-1-propanesulfonate), CHAPSO (3-[(3-cholamidopropyl)dimethylammonio]-2-hydroxy-1-propanesulfonate), and octyl glucoside (e.g., (2R,3S,4S,5R,6R)-2-(hydroxymethyl)-6-octoxyoxane-3,4,5-triol).

"Ureide" refers to a cyclic or acyclic organic molecule of natural or synthetic origin that comprises one or more urea moieties or derivatives thereof. In certain embodiments, the invention provides ureides such as urea, uric acid, hydantoin, allantoin (CAS number 97-59-6; alcloxa, aldioxa, hemocane, ureidohydantoin, 5-ureidohydantoin, glyoxylureide, glyoxylic acid diureide, 2,5-dioxo-4-imidazolidinyl urea), purines, and derivatives thereof. In certain embodiments, the invention provides organic molecules of the formula R—CO—NH—CO—NH$_2$ or R—CO—NH—CO—NH—CO—R' or R'R"NH—CO—NR'"R"" where the relevant "R-groups" may be H or any organic moiety.

"Virus" or "virion" refers to an ultramicroscopic (roughly 20 to 300 nm in diameter), metabolically inert, infectious agent that replicates only within the cells of living hosts, mainly bacteria, plants, and animals: composed of an RNA or DNA core, a protein coat, and, in more complex types, a surrounding envelope.

In certain embodiments, an antibody can be eluted in the same buffer to which the column is equilibrated prior to sample application. In such embodiments the invention can provide an advantage that it can be used for the purpose of exchanging the buffer in which the sample resides, from its initial formulation to a formulation more suitable for subsequent processing by other methods. While the composition of buffer in which the sample initially resides is unrestricted except by the need to avoid damaging the antibody, the composition of the column equilibration buffer must be within a range that does not create negative charge on the antibody at a level sufficient to cause a substantial proportion of the antibody to bind to the positively charged particles. Appropriate equilibration conditions vary according to the choice of positively charged porous particles and the particular features of specific antibodies. In general, column equilibration conditions may range from but are not limited to conductivity values of less than 0.1 mS/cm to more than 30 mS/cm, and pH values from less than 4.0 to greater than 9.0.

In certain embodiments where it is an objective of the technique to reduce contaminant levels, it will be advantageous to employ the highest pH and/or the lowest conductivity that does not cause the antibody to bind substantially to the positively charged particles. It will be understood that the guidelines of highest pH and/or lowest conductivity may be moderated according to the solubility and stability requirements of the antibody.

In certain embodiments, where the electropositive particles bear additional chemical functionalities, it may be necessary or beneficial to employ lower pH values or include additives that modulate the interactivity of the antibody with the surface of the particles in order to practice the method. The simplest such variant may be to add NaCl or other salts. The most effective level can be determined experimentally by evaluating different increments of NaCl concentration, such as 25 mM, 50 mM, 100 mM, 200 mM etc. Once the effective range is determined, it may be refined with subsequent experiments conducted at finer increments or by means of statistical methods such as so-called Design of Experiments (DoE). Alternative salts may also be considered, as well as other additives including sugars, chaotropes, organic solvents, and surfactants, among others. Combinations of additives may also be evaluated, including in combination with various pH values.

In certain embodiments, the positively charged particles residing within the column may be of a single type or of multiple types, including combinations of porous and nonporous particles, or combinations of porous particles with different pore sizes. Where the invention employs a combination of particles with pores of different sizes, one subset of particles may have pores of a size that physically excludes antibody, while another subset may have a pore size that does not exclude antibody. In such a case, the subset with pores large enough to not exclude antibody may present the ligand in such a way as to physically hinder pore entry by antibodies lacking a strong negative charge.

In certain embodiments, the method's buffer exchange capability provides the advantage that it particularly removes low molecular weight sample components that might interfere with subsequent processing methods. This reveals another unexpected feature of certain embodiments of the invention. Since ethacridine, a highly effective aggregate-dissociating agent, it is expected to be repelled from the surface of the positively charged porous particles. However, it does not co-elute with the IgG antibody. While other positively charged additives, such as polyethyleneimine and other cationic polymers are repelled as expected and in certain embodiments do co-elute with the IgG, they can be selectively retained relative to the IgG by mixing a small increment of negatively charged particles with the electropositive porous particles in the column.

In certain embodiments, the methods of the invention may be applied with equal effectiveness to the purification of IgG fragments such as Fab and F(ab')$_2$, as well as minibodies, diabodies, so-called single chain VHH domains, Fc-fusion proteins and other IgG-derivative constructs that may embody charge properties similar to IgG.

In certain embodiments, the invention may be used for the initial fractionation of antibody from crude samples, or at any stage of purification; in any case illustrating that the invention may be combined with other purification methods to achieve the overall degree of purification required for a particular antibody application.

It will be apparent to the person of ordinary skill that the invention will also confer the benefits of achieving highly effective reduction of host cell proteins, DNA, endotoxin, and virus, either with or without the inclusion of aggregate-dissociating and or virus precipitating or inactivating agents in the sample. It will be equally apparent that the removal of these contaminants will be further enhanced when the formulation of the elution buffer falls within the recommended ranges of the column equilibration buffer. This will require the subsequent application of a cleaning buffer to remove still-bound DNA, endotoxin, and/or virus from the column, if the column is intended to be used for multiple cycles.

Additional objects and advantages of the invention will be set forth in part in the description which follows, and in part will be obvious from the description, or may be learned by practicing the invention. The objects and advantages of the invention will be realized and attained by means of the elements and combinations specified in the claims.

It is to be understood that both the foregoing general description and the following detailed description are exemplary and explanatory only and are not restrictive of the invention as claimed.

In preparation for using certain embodiments of the invention, the usable sample volume with respect to the column must be determined. In its simplest mode, where all of the particles in the column are positively charged porous particles, this value may be estimated by multiplying the total volume of an uncompressed gravity-settled packed chromatography bed by 0.4. Permissible maximum sample volume may be determined precisely by a simple experiment in which the column is equilibrated to a low salt buffer at a moderate pH, and a sample of IgG in a high salt buffer is applied, then followed with additional equilibration buffer. Mark the point at which antibody begins to elute, as indicated by an increase in UV absorbance at 280 nm. Mark the point at which the high salt begins to elute, as indicated by an increase in conductivity. The volume between the marks represents the maximum sample volume per cycle for that column.

Suitable sample volumes for the performance of certain embodiments of the invention for columns that include additional particles other than porous electropositive particles (such as those bearing secondary chemical surfaces) can be estimated by multiplying the volume of only the positively charged porous particles. The above experiment can be applied to specifically define the maximum sample. It will be apparent that the maximum sample volume for a given column of mixed positive and other particles will be reduced from exclusively positive porous particle columns in proportion to the relative column volume occupied by the non-positive particles.

In certain embodiments, development of a method for purification of a particular antibody will generally begin with evaluation of the simplest option, which will be a column packed exclusively with positively charged porous particles. Appropriate particles may consist of commercial chromatography media marketed for practicing the technique of so-called anion exchange chromatography. Examples of the dozens of such products include Capto-Q, Capto DEAE, QAE Sephadex, DEAE Sephadex (GE Healthcare); GigaCap Q and Q-Toyopearl (Tosoh Bioseparations); Macroprep DEAE, Macroprep High-Q, UNOsphere Q, and Nuvia Q (Bio-Rad Laboratories); Eshmuno Q, DEAE Fractogel, TMAE Fractogel (Merck); and Q-HyperD (Pall). Such products are not at present labeled with respect to the identity or concentration of secondary functionalities on their surfaces, nor the pore size, nor exclusion limit, nor virtual pore size resulting from their respective employment of ligand grafting methods to enhance their functionality, nor is such information generally available from suppliers. It should be anticipated that all such products include multiple physical and chemical functionalities, and that it will be prudent to evaluate more than one product to determine which is inherently most suitable for purification of a particular antibody. In one embodiment, evaluation may begin with UNOsphere Q and Nuvia Q, or only UNOsphere Q.

For any given antibody, it will be advisable to evaluate a range of pH and conductivity values to which the column is initially equilibrated. As a general matter, aggregate and contaminant reduction are best at the highest pH and lowest conductivity at which the antibody remains soluble and stable, so initial conditions of a slightly alkaline buffer such as 20-50 mM Tris, pH 8.0, may be a convenient place to start. Lower and higher pH values may be subsequently evaluated, with pH values as low as 2.0 or higher than 9.0, and conductivity values ranging from less than 0.1 to more than 30 mS/cm.

It may be useful in some embodiments to evaluate conditions that render the eluted sample suitable for application to a subsequent purification step without requirement for further sample preparation. For example, if the eluted sample is to be applied subsequently to a cation exchange column at a pH of 6.0, it may be desirable to equilibrate the column to a pH 6.0. If the eluted sample is to be applied subsequently to a hydroxyapatite column, it may be suitable to employ neutral pH and set the phosphate concentration of the buffer at the level required by the hydroxyapatite column, and to omit chelating agents such as EDTA or citrate. In any case where the equilibration buffer is selected for continuity with a subsequent fractionation method, high pH low conductivity conditions will still be generally evaluated to ensure that purification potential is not sacrificed in the present step.

Without being bound to any particular theory, it is believed that the method is virtually independent of sample composition. Consequently, in certain embodiments, the sample may contain a variety of agents, individually or in combination, to enhance dissociation of antibody aggregates or antibody-contaminant complexes, or to reduce DNA, endotoxin, or virus contamination. Such agents may include, in certain embodiments, up to 8 M urea, up to 6 M guanidine, reducing agents, surfactants, organic solvents, ethacridine, chlorexidine, benzalkonium chloride, tri(n-butyl)phosphate, and methylene blue, among others. The limiting factor in these cases will be that the added agents do not damage or precipitate the antibody. Agents such as ethacridine and chlorhexidine may be effectively applied at concentrations ranging from less than 0.001% to 1%, depending on the characteristics of the antibody and the composition of the sample. As a general matter, low concentrations will be preferred in most cases because high concentrations may cause the formation of precipitates, which could require an additional step to remove them before applying them to the column of electropositive porous particles. Experimental data on UNOsphere Q reveal concentrations of 0.01 to 0.05 to fulfill this ideal, and particularly concentrations ranging from 0.020 to 0.025%.

In certain embodiments where the antibody in the sample has been treated previously with agents as described above; or if the method is to be practiced on samples of unpurified cell culture supernatant, the performance of the method may be enhanced by using positively charged porous particles that embody substantial secondary functionalities. Examples may include porous particle-based commercial chromatography products that embody positive charges deliberately combined with secondary functionalities. Such media are commonly referred to as mixed modes. Capto adhere (GE healthcare) is an example of a commercial mixed mode chromatography product combining positive charges with functionalities that confer the ability to participate in hydrophobic interactions, pi-pi bonding, and hydrogen bonding. Similar combinations are known in the literature and additional commercial entries can be expected. It will be apparent to the skilled person in the art that the formulation of the equilibration buffer may need to be modified to prevent retention or retardation by the secondary functionalities. In the case of Capto adhere, for example, it may be necessary to operate at a lower pH and higher conductivity than would be required with chromatography media marketed for anion exchange. Inclusion of secondary functionalities does not however impair the ability of the invention to accommodate samples without respect to sample composition, including extremely high conductivity that is well understood in the field to interfere directly and dramatically with the function of other methods exploiting charged chromatography surfaces, including positively charged chromatography surfaces.

In certain embodiments where the sample includes compositions such as described above, it may alternatively be useful to combine porous electropositive particles with distinct particles that embody secondary chemical functionalities, and pack the two or several particle types together in the same column. Particles bearing secondary functionalities may be porous or non-porous. As above, the method remains independent of sample composition. Likewise, equilibration conditions may be limited by the need to suspend interactions between the antibody and the secondary functionalities. For example, if particles bearing a negative charge functionality are present and a particular antibody has a strong tendency to bind such charges, it may be necessary to increase pH and/or conductivity. The favorable trade-off in this case as above, is that the inclusion of one or more secondary functionalities may enable a higher degree of purification.

In certain embodiments where porous electropositive particles are combined with distinct particles that embody secondary functionalities, the latter may be layered on top of the bed of electropositive particles or packed in a separate column that may be plumbed immediately before or immediately after the column of electropositive particles. In some embodiments, the porous electropositive particles are mixed with separate particles bearing secondary functionalities.

When developing particle mixtures to optimize purification of a particular antibody for certain embodiments of the invention, the secondary functionalities may be selected to accommodate an elevated presence of a particular type of contaminant. For example, a hydrophobic secondary functionality may improve efficiency of removal for hydrophobic but uncharged components such as tri(n-butyl)phosphate. Electronegative functionalities may improve the efficiency of removal for positively charged agents such as ethacridine. Combinations of electronegative-hydrophobic secondary functionalities may improve removal efficiency of positively-charged hydrophobic contaminants such as ethacridine, benzalkonium chloride, and methylene blue. Experimental data suggest that the improvement in such cases does not reflect the native inability of the invention to remove these contaminants when they exist independently in the sample; rather, they suggest that enhanced functionality derives from their ability to competitively dissociate these agents from otherwise stable complexes with the antibody, and/or the ability of the secondary functionality to remove amounts of contaminants that could saturate and neutralize the positive charge on the primary particles that is required to repel the antibody into the inter-particle space. In certain alternate embodiments, the method may be practiced such that the secondary particles may be added directly to the sample in advance to scavenge the potentially troublesome contaminants and the particles are then separated from the sample such that the partially purified sample is then contacted with the column.

When developing particle mixtures to optimize purification of a particular antibody, the secondary functionalities may be selected alternatively or in addition according to their ability to enhance pH control and/or reduce buffer volumes required to titrate the column to its desired operating pH. For example, anion exchangers are known to produce uncontrolled temporary pH increases when exposed to elevated conductivity. They produce uncontrolled temporary pH reductions when conductivity is reduced. The magnitudes and durations of these effects vary with the conductivity differential between steps, the charge characteristics of the exchanger, and buffer capacity. Cation exchangers suffer the same problem but the direction of the uncontrolled pH excursions is opposite to those that occur with anion exchangers. Combining a secondary electronegative functionality with a primary electropositive functionality thus reduces the magnitude and duration of pH excursions. The ideal mix of functionalities may be readily determined by experimentation.

In certain embodiments employing additional particles with functionalities distinct from the electropositive particles, and where those distinct particles are mixed with or packed in a column preceding the electropositive particles, it may be necessary to adjust the initial sample down from the amount that would be applied to a column of exclusively electropositive particles to account for the increase in sample volume that occurs as a result of dispersion of the antibody as it diffuses into and out of the pores in the distinct particles. The necessary degree of reduction of initial sample volume, if any, may be easily determined by simple experimentation, where the criterion is the elution of the antibody within the equilibration buffer.

In certain embodiments, the method is distinguished from other applications of positively charged porous particles due to its effectiveness being independent of the composition of the buffer applied immediately after sample application. In many instances, it will be advantageous to follow the sample application immediately with a buffer composition intended to completely elute materials bound to the porous particles. For example, a column may be equilibrated to roughly physiological conditions, such as 50 mM Hepes, 0.1 M NaCl, pH 7.0. Antibody cell culture supernatant containing 1.0 M sodium chloride, pH 8.0, is applied in a volume amounting to 35% of the column volume, then followed with 2 M sodium chloride, pH 4.0. The substantially purified antibody elutes in the physiological Hepes-saline buffer. This occurs because the antibody travels exclusively through the inter-particle space, as described above, while chase-buffer must also travel through the intra-particle pore space. The compelling feature of this approach is that it supports the unique ability to elute contaminants and clean the column simultaneously, with the practical benefit of shortening the process cycle, reducing process time and material usage. This makes it attractive to perform multiple cycles on a small column rather than a single cycle on a large column, which further reduces material usage.

In certain embodiments, it may be advantageous to follow the sample with equilibration buffer, or a buffer of lower conductivity, for example 50 mM Tris, pH 8.0, for the express purpose of enhancing retention of acidic contaminants with a hydrodynamic size greater than the average pore diameter of the electropositive porous particles, such as virus, since they may otherwise elute at the trailing boundary of the antibody and potentially contaminate it to an excessive and unnecessary degree. To the extent that the column may include an increment of electronegative particles, this may also enhance removal of electropositive contaminants. The ideal volume of low-conductivity chase-buffer may be determined experimentally, beginning with about 50% of the packed column volume.

In certain embodiments, the method supports faster flow rates than are generally used for chromatography on porous particles. This is because the antibody travels exclusively through the inter-particle space where mass transport is convective, and is therefore not affected by the slow diffusion constant of the antibody, nor by flow rate or sample viscosity. Thus the method can be practiced with high efficiency at linear flow rates up to 1000 cm/hr or more, versus usual porous particle chromatography operations that are carried out at 150-300 cm/hr. Flow rates above 300 cm/hr however may require a reduced sample volume. This is because mass transport for unbound contaminants is diffusive, becoming less efficient with increasing flow rate or sample viscosity. Excessive flow rates afford less opportunity for contaminants to achieve diffusive equilibrium with the pores of the porous particles. Experimentation will reveal the ideal flow rate for any given antibody and set of buffer compositions.

In certain embodiments where the electropositive porous particles are combined in a column of porous particles bearing other surface chemistries, it will generally be useful to base the maximum sample volume on the volume of the electropositive particles only. Even then, it may be prudent to determine maximum sample volume experimentally since the presence of particles lacking an electropositive surface may have the effect of diluting the sample within the column.

In certain embodiments, particles bearing surface chemistries other than electropositivity may be packed in a separate column that is plumbed in series with the column of electropositive particles. In such a configuration, the same cautions may be applied as those discussed for the situation where other-chemistry particles are mixed in the same column with electropositive particles.

In certain embodiments, methods disclosed herein may be used for the initial purification step following sample preparation. In other embodiments, it may be used for intermediate purification, or it may be used for final purification. It will be apparent to those skilled in the art that in any case where the method is not used as the last step in a process, it has the ability to facilitate overall process continuity by virtue of its ability to buffer exchange the sample coincident with reduction of aggregates and/or contaminants.

In certain embodiments, the invention may be practiced in conjunction with other purification methods. Specifically, it may be used in any combination with size exclusion, anion exchange, cation exchange, hydrophobic interaction, preferential exclusion, hydroxyapatite or other forms or mixed mode chromatography, or bioaffinity chromatography; also in conjunction with precipitation, crystallization, and methods of aqueous two-phase partitioning.

After obtaining the processed IgG, the contents of the column may be discarded. Alternatively, the column may be cleaned with high concentrations of salt then restored to original conditions by re-equilibration so that it may be used for additional cycles. The column may also be sanitized with appropriate agents such as sodium hydroxide.

In certain embodiments, the invention may be mechanized and automated to increase throughput. In certain such embodiments, for example, the method may include an automated multicolumn system such as used to perform simulated moving bed chromatography.

In certain embodiments, methods disclosed herein may be applied effectively to non-antibody proteins, particularly including proteins with an alkaline isoelectric point such as certain plasma proteins like complement C1q and inter-alpha trypsin inhibitor, or histones. In the case of histones, the present methods are especially advantageous since the sample can be combined with one or more strong chemical dissociating agents such as but not limited to a high concentration of guanidine, to separate the histones from DNA and other contaminants from which they may be associated. The equilibration buffer can then be chosen according to the same guidelines as for antibodies. These non-IgG applications also reveal the suitability of the method for purification of other proteins, where the protein of interest is the most alkaline component in the mix, or among the most alkaline component in a mix, or more alkaline than at least one particular contaminant, so that conditions can be developed where the protein of interest passes convectively through the void volume while the contaminant or contaminants travel diffusively through the pore volume of the particles or are bound to the particle surfaces.

EXAMPLES

Example 1

A 10 mL column was packed with electropositive porous particles (Nuvia Q, Bio-Rad Laboratories) and equilibrated with 50 mM histidine, pH 7.5. 2 mL of clarified cell culture supernatant containing about 2 mg of monoclonal IgG (clone her2) containing more than 20% aggregates was applied to the column at a flow rate of 300 cm/hr. A protein peak eluted in equilibration buffer, then a large amount of material flowed through as the buffer in which the sample was applied passed through the column. The column was eluted with a step to 50 mM Hepes, 2 M sodium chloride, producing a concentrated contaminant peak. pH was stable during elution of the initial peak but increased to pH 8.1 during the passage of the flow through material, then jumped to about pH 8.7 at the beginning of the salt elution step. The initial peak, subsequent flow-through, and elution peak were analyzed by size exclusion chromatography. The initial peak contained about 80% pure IgG with an aggregate concentration below 0.1%. The contaminants mostly comprised free excess antibody light chains. IgG recovery was estimated at greater than 95%. The subsequent flow-through material contained host cell proteins and small-molecule cell culture media components. The elution peak contained DNA, some host protein contaminants, and cell culture media components. IgG was absent from the later flow-through and salt elution fractions.

Example 2

A 10 mL column was packed with electropositive porous particles (UNOsphere Q, Bio-Rad Laboratories) and equilibrated with 50 mM histidine, pH 7.2. 2 mL of clarified cell culture supernatant containing about 2 mg of monoclonal IgG (clone her2) containing more than 20% aggregates was applied to the column at a flow rate of 300 cm/hr. A protein peak eluted in equilibration buffer, then a large amount of material flowed through as the buffer in which the sample was applied passed through the column. The column was eluted with a step to 50 mM Hepes, 2 M sodium chloride, pH 7.0, producing a concentrated peak. The initial peak, subsequent flow-through, and elution peak were analyzed by size exclusion chromatography. The initial peak contained about 80% pure IgG with an aggregate concentration below 0.1%, and about 20% free excess antibody light chains. The subsequent flow-through material contained host cell proteins and small-molecule cell culture media components. The elution peak contained DNA, some host protein contaminants, and cell culture media components. IgG was absent from the later flow-through and salt elution fractions.

Example 3

A column was packed with electropositive porous particles (5 mL each of Nuvia Q and UNOsphere Q) then equilibrated with 50 mM Hepes, pH 7.0. 2 mL of clarified cell culture supernatant containing about 2 mg of monoclonal IgG (clone her2) containing more than 20% aggregates was applied to the column at a flow rate of 300 cm/hr. A protein peak eluted in equilibration buffer, then a large amount of material flowed through as the buffer in which the sample was applied passed through the column. The column was eluted with a step to 50 mM Hepes, 2 M sodium chloride, producing a concentrated peak. The initial peak, subsequent flow-through, and elution peak were analyzed by size exclusion chromatography. The initial peak contained about 80% pure IgG with an aggregate concentration below 0.1%, and about 20% free excess antibody light chains. The subsequent flow-through material contained host cell proteins and small-molecule cell culture media components. The elution peak contained DNA, some host protein contaminants, and cell culture media components. IgG was absent from the later flow-through and salt elution fractions.

Example 4

The experiment of Example 3 was repeated except equilibrating the column with 50 mM Hepes, 50 mM NaCl, pH 7.0. Recovery and composition of the initial peak was equivalent to those obtained in Example 3.

Example 5

The experiment of Example 3 was repeated except equilibrating the column with 50 mM Hepes, 100 mM NaCl, pH 7.0. Recovery and composition of the initial peak was equivalent to those obtained in Example 3.

Example 6

The experiment of Example 3 was repeated except equilibrating the column with 50 mM Hepes, 150 mM NaCl, pH 7.0. Recovery and composition of the initial peak was equivalent to those obtained in Example 3. The results of Examples 3-6 surprisingly showed that IgG purity and recovery obtained in the initial peak did not go down with increasing salt concentration of the equilibration buffer. Subsequent experiments revealed that recovery and purity were also surprisingly little-affected by reducing the operating pH to 6.0 (50 mM MES). Neither was performance significantly improved at pH 8.0 (50 mM Tris).

Example 7

A column was packed with 10 mL of electropositive porous particle media (Macroprep High-Q), and equilibrated with 50 mM Hepes, pH 7.0. 2 mL of clarified cell culture supernatant containing about 1 mg of monoclonal IgG (her2) was applied at a linear flow rate of 300 cm/hr. A protein peak began to elute in the equilibration buffer. The remainder of the peak exited the column with the salts from the original sample, and also contained the pH indicator dye phenol red. Greater than 95% pure IgG was found in both peaks. All other contaminants eluted later with continuing flow of equilibration buffer, and with elution by 50 mM Hepes, 2 M NaCl, pH 7.0. This illustrates differences in separation performance among different electropositive media.

Example 8

A column was packed with 10 mL of the electropositive porous particles (UNOsphere Q) mixed with 2 mL of chelating porous particles that also include strong electronegative, hydrogen bonding and hydrophobic functionalities (Chelex-100). The column was equilibrated with 50 mM Hepes, 200 mM NaCl, pH 7.0 (conductivity 21 mS/cm). 2 mL of clarified cell culture supernatant about 2 mg monoclonal IgG (clone her2) was applied to the column at a flow rate of 300 cm/hr. A protein peak eluted in the equilibration buffer, then a large amount of material flowed through with the buffer in which the sample was applied. A large peak was subsequently eluted in 50 mM Hepes, 2 M NaCl. Analytical SEC revealed the initial peak to be greater than 95% pure IgG with an aggregate content less than 0.1%. Antibody recovery was greater than 95%. The experiment was repeated several times, at conductivity values of 11, 16, and 31 mS/cm. Performance was identical at all conductivity values of 21 mS/cm and below. Aggregate reduction was identical at 31 mS but the slope on the ascending side of the IgG peak was shallower and recovery was reduced to 90%.

Example 9

Dissolved ethacridine from a 1% solution in water was added stirring to 10 mL of cell culture media containing an IgG monoclonal antibody (clone her2), producing a strong yellow 0.02% ethacridine solution. The column of Example 8 was equilibrated with 50 mM histidine, pH 7.5. 2 mL of the yellow colored but optically clear supernatant was applied to the column and collected. The column was then eluted with 25 mM Hepes, 3 M NaCl, pH 7.0, then cleaned with 25 mM Hepes, 3 M guanidine, pH 7.0. The initial peak, eluting in equilibration buffer, was collected. This fraction plus a sample of the ethacridine treated material were analyzed by SEC. More than 95% of the IgG was recovered in the first peak at a purity of about 80%, and aggregate content less than 0.1%. Column elution with 3 M NaCl removed a large body of contaminants but ethacridine remained bound to the column and was subsequently removed with guanidine.

Example 10

50 mg of ethacridine was added stifling to 10 mL of cell culture media containing an IgG monoclonal antibody (clone her2), yielding a 0.5% solution. This caused immediate formation and sedimentation of a dense yellow precipitate that was removed by filtration. The column of Example 8 was equilibrated with 50 mM histidine, pH 7.5. 2 mL of the yellow colored but optically clear supernatant from the ethacridine treatment was flowed over the column and collected. The column was then eluted with 25 mM Hepes, 3 M NaCl, pH 7.0 then cleaned with 25 mM Hepes, 3 M guanidine, pH 7.0. The initial peak, eluting in equilibration buffer, was collected. This fraction plus a sample of the ethacridine treated material were analyzed by SEC, and compared with results from examples above. The high concentration of ethacridine caused a 23% reduction in IgG recovery, and less than 5% improvement in purity, but aggregate content was still reduced to less than 0.1%, and the ethacridine content of the IgG as indicated by UV absorbance at 365 nm was nil.

Example 11

105 mL of IgG-containing cell culture supernatant was prepared in a series of process cycles each consisting of equilibrating a 60 mL column of UNOsphere Q with 50 mM Hepes, 100 mM NaCl, pH 7.0, applying 15 mL of sample, then applying 50 mM Hepes, 2 M NaCl, pH 7.0. The processed IgG was subsequently applied to a column of immobilized protein A for performing affinity chromatography. Results of the protein A purification were compared to results from an untreated sample consisting of 105 mL of filtered cell culture supernatant. The material treated by the invention contained more than 10-fold lower DNA and host cell protein contaminants.

Example 12

An IgG antibody initially purified by constrained cohydration chromatography followed by cation exchange chromatography was processed by the invention, on a column of UNOsphere Q equilibrated in 50 mM Tris, pH 8.0. Results were compared with a sample that was processed by flow-through chromatography on UNOsphere Q. Host cell protein content of the material processed by the invention was 8-fold lower than the material processed by flow-through chromatography. Relative improvement for DNA removal was not possible to calculate because DNA levels were below the detection limit of the assay in the sample processed by the invention. DNA was measured at about 23 parts per million in the sample processed by flow-through chromatography.

Example 13

IgG antibody (her2) purified by the invention from cell culture supernatant on UNOsphere Q equilibrated to 50 mM Hepes, 100 mM NaCl, pH 7.0 was applied to a column of hydroxyapatite (CHT type I, 40 micron) and eluted with a phosphate gradient. This eliminated the free light chain contaminants, leaving the antibody at close to 99% purity.

Example 14

IgG antibody (her2) purified by the invention from cell culture supernatant on UNOsphere Q equilibrated to 50 mM Hepes, 100 mM NaCl, pH 7.0 was diluted with 4 parts 50 mM MES, pH 6.0, applied to a cation exchanger (Nuvia S), and eluted in a salt gradient at pH 6.0. This eliminated the free light chain contaminants, leaving the antibody at close to 99% purity.

Example 15

An *E. coli* lysate containing an IgG Fab protein was applied to a column of UNOsphere Q equilibrated to 50 mM Hepes, 100 mM NaCl, pH 7.0. More than 90% of the protein contaminants as visualized by SDS polyacrylamide gel electrophoresis were removed from the Fab.

Example 16

The suitability of various commercial anion exchangers was evaluated. Individual 1.6 cm diameter columns were packed with 20 mL of each of the following media: UNOsphere Q, Nuvia Q, Capto Q, GigaCap Q, Poros HQ, Q Fast Flow Sepharose, and Fractogel tentacle DEAE. Each column was equilibrated to 50 mM Tris, pH 8.0. A sample of purified Herceptin IgG in 50 mM Hepes, 100 mM NaCl, pH 7.0, amounting to 5 mL, was applied to each. Complete void partitioning of IgG was observed for UNOsphere Q and Nuvia Q. Partitioning was about 95% for Capto Q and about 85% for GigaCap Q. Partitioning was about 75% for Fractogel DEAE, 65% for Q Sepharose, and 50% for POROS HQ.

Example 17

The breadth of applicability was determined by applying samples of different antibodies and fragments to a column of UNOsphere Q equilibrated with 50 mM Tris, pH 8.0. The samples consisted of purified IgG monoclonal antibodies including Herceptin, Rituxan, Avastin, and Humira. All portioned effectively except Avastin. The column was re-equilibrated with 50 mM Tris, 100 mM NaCl, pH 8.0, in which all antibodies partitioned effectively.

Example 18

Breadth of applicability was evaluated further by applying Fab and F(ab')$_2$ fragments from Rituxan to the column described in Example 17. Both partitioned effectively in 50 mM Tris, pH 8.0. Application of the Fab sample, which also contained residual Fc fragments following the process of enzymatic digestion, also provided the additional advantage of removing the Fc fragments, by virtue of them binding to the exchanger and being subsequently eluted by an elevation of NaCl concentration.

Example 19

Breadth of applicability was evaluated further by applying a monoclonal IgM antibody to the column described in example 17. This IgM had an isoelectric point above 9.0, which suggested that it should partition well in 50 mM Tris, pH 8.0. It did not do so, but did partition effectively when 200 mM NaCl was included in the equilibration buffer. This was attributed to uneven charge distribution on the antibody, which may also explain why Avastin (Example 17) did not partition fully in 50 mM Tris, pH 8.0.

Example 20

Two-step purification of Herceptin. Application of unpurified herceptin to the a column of UNOsphere Q equilibrated with 50 mM Tris, pH 8.0 resulted in the greater than 99% removal of contaminating host-cell proteins and DNA, but co-elution of excess free light chain with the antibody. Free light chain was removed by cation exchange chromatography, hydroxyapatite chromatography, or mixed mode chromatography on Capto adhere. In the case of cation exchange chromatography, the light chain was removed in a NaCl gradient applied at pH 6.0, with the cation exchange step being run either before or after the invention. In the case of hydroxyapatite, the light chain was removed in a phosphate gradient. In the case of Capto adhere, the light chain was removed by binding the sample in 50 mM Hepes, 1 M NaCl, pH 7.0 then eluting the column with a linear gradient in which NaCl concentration was reduced to an eventual concentration of zero.

Example 21

Examination of pH and conductivity conditions. The partitioning behavior of purified herceptin was evaluated over pH values ranging from 3.0 to 10.0, and NaCl concentrations ranging from 0 to 2 M. These experiments were conducted on UNOsphere Q. In the absence of added NaCl, herceptin partitioned at all pH values up to and including pH 8.0. It partitioned at all pH values in the presence of 50 mM NaCl or higher. The purification potential of the method was evaluated by applying unpurified herceptin at pH values ranging from 4-8, and NaCl concentration from 0 to 4 M. The best purification performance was obtained at the highest pH and lowest conductivity. Greater than 99% reduction of host cell proteins, DNA, endotoxin, and virus was obtained at 50 mM Tris pH 8.0. Antibody recovery was also greater than 99%. Decreasing pH in the absence of NaCl resulted in reduced contaminant reduction. Increasing NaCl concentration at pH 8.0 also resulted in reduced contaminant reduction.

Example 22

Combination of electropositive porous particles with hydrophobic negatively charged particles. A 20 mL column of UNOsphere Q was plumbed in line directly following a 5 mL column of Macroprep T-butyl, which is believed to embody a combination of hydrophobic and cation exchange functionalities. A cation-exchange processed sample of herceptin was applied. An identical sample was applied to a column of UNOsphere Q only. The host cell protein content of the sample purified by the tandem columns was 44% lower than the sample applied exclusively to UNOsphere Q (1559 parts per million (ppm) versus 2822 ppm). In a subsequent series, varying percentages of Macroprep T-Butyl were combined directly with UNOsphere Q: 0.5%, 1% and 1.5%. No significant improvement was apparent.

Example 23

Multistep antibody purification. Herceptin was purified from clarified cell culture supernatant by treatment with 1% allantoin in the presence of 0.025% ethacridine, followed by filtration through a mixture of particles substituted with tris(2-aminoethyl)amine and iminodiacetic acid, then initial antibody capture by steric exclusion chromatography in polyethylene glycol, followed by cation exchange, followed by the claimed invention. The host protein concentration after the cation exchange step was 17 ppm. The present invention, applied at pH 8.25 in 50 mM Tris, reduced the host protein concentration to 2 ppm. The process was repeated, except substituting steric exclusion chromatography in ammonium sulfate. Host protein concentration after cation exchange was 158 ppm. The present invention applied at pH 8.25, reduced host protein to 9 ppm. Purification of the same antibody by protein A reduced the host protein concentration to 123 ppm. The claimed invention reduced it from 123 ppm to 3 ppm. The majority of the ethacridine was removed by the iminodiacetic acid. Ethacridine was undetectable in the final material.

Example 24

Multi-step purification of IgG. The procedure of example 23 was followed except reducing the pH of the cell culture supernatant to 5.5 and substituting 0.1% octanoic acid for ethacridine. After flowing the sample through the column of tris(2-aminoethyl)amine and iminodiacetic acid, the sample was titrated to pH 8.0 for the steric exclusions step. The majority of the octanoic acid was removed by the immobilized tris(2-aminoethyl)amine. Octanoic acid was undetectable in the antibody after the final step.

Example 25

Removal of antiviral compounds from antibody preparations. In separate experiments, 0.025% ethacridine was added to purified Herceptin at pH 8.0, and 0.1% octanoic acid was added to purified herceptin at pH 5.5. The samples were processed by applying a sample constituting 35% of the volume of a column of UNOsphere Q equilibrated to 50 mM Tris, pH 8.25. Ethacridine bound strongly to the column as shown by the accumulation of an intense yellow band at the top. Octanoic acid was similarly removed, though not evident visually due to its colorless nature. In both cases, the column was regenerated by elution of 3 M guanidine, pH 5.5.

Example 26

Use of multimodal positively charged particles. A partially purified sample of monoclonal anti-her2 IgG containing 589 parts per million of contaminating host cell proteins, of a volume of 4 mL in 50 mM MES, 25 mM NaCl, pH 6.0, was applied to a 20 mL column of Capto adhere equilibrated to 50 mM acetate pH 4.0. About 92% of the antibody partitioned to the void volume. Host protein content of the partitioned IgG was 5 parts per million, representing a reduction of about 99%. Antibody recovery was about 92%. The operating conditions were chosen from a range of pH and salt conditions screened as described in Example 21. The highly disparate conditions between this Example and Example 21 highlight that the method works among a wide range of chemical selectivities so long as a positive charge is present. The two Examples also highlight the utility of the method across a range of chromatography media types, and the ability of simple but systematic screening to identify the most appropriate conditions.

Example 27

Use of positively charged microporous particles. A partially purified 4 mL sample of herceptin in 50 mM Hepes, 50 mM NaCl, pH 7.0 was applied to a column containing 20 mL of QAE Sephadex A25 equilibrated to 50 mM Tris, pH 8.0. The chromatogram indicated that antibody eluted in the void volume, but salts also began to elute in the void. It was hypothesized that salt elution in the void occurred because of ion exclusion of the sodium ions from the salt in the original sample. 45 ppm of host cell protein also eluted with the antibody. The experiment was repeated in several iterations with increasing salt concentration in each of the iterations. The sample-salt peak was more confined to the included volume with increasing equilibration salt concentration, so that at 200 mM NaCl, the elution profile was essentially the same as observed with UNOsphere Q. This appears to be consistent with the ion exclusion hypothesis. Surprisingly, removal of contaminants also increased with increasing equilibration salt, to the point that no host protein contaminants were detected at 200 mM NaCl. Thus, the operating characteristics of this particle material follows exactly the opposite response to increasing salt observed with UNOsphere Q. On no occasion did UNOsphere Q exhibit early elution of salt ions such as observed with QAE Sephadex. Host cell proteins in this experiment were measured by ELISA.

Example 28

Use of ligand-grafted positively charged particles.

GENERAL EXPERIMENTAL CONDITIONS

Buffers, salts, and reagents were obtained from Sigma-Aldrich (St. Louis, Mo.). A rat IgM hybridoma, clone 60A9, was produced in 5% fetal bovine serum by SP2/0 cells. Chimeric and humanized biosimilar IgG monoclonal antibodies were produced in protein-free media by Chinese hamster ovary cells, employing a tricistronic vector (Ho et al., *J. Biotechnol.* (2012) 157:130-et seq.). Rituximab F(ab')$_2$ and Fab were prepared by digestion with immobilized enzymes (Gagnon et al., *J. Sep. Sci.* (2009) 32:3857-et seq.).

UNOSPHERE™ Q, NUVIA™ Q, and ceramic hydroxyapatite CHT™ type 140 μm were purchased from Bio-Rad Laboratories (Hercules, Calif.). GIGACAP™ Q was purchased from Tosoh Bioscience (Tokyo, Japan). Fractogel DEAE Hi-Cap was purchased from Merck (Darmstadt, Germany). Q SEPHAROSE™ Fast Flow, CAPTO™ Q, Capto adhere, MABSELECT™ (protein A) and SEPHADEX™ G25 were purchased from GE Healthcare, (Uppsala, Sweden). POROS® HQ-50 and XS were obtained from Applied Biosystems (Foster City, Calif.). CIM™ QA monoliths were obtained from BIA Separations (Klagenfurt, Austria). SARTOBIND™ Q-Nano membrane filtration units were obtained from Sartorius-Stedim (Goettingen, Germany). PROSEP™-Va (protein A) was purchased from Millipore (Billerica, Mass.).

Particle-based media for anion exchange were packed in XK™16/20 columns (20 mL, 10 cm bed height; GE Healthcare) at a linear flow rate of 300 cm/hr. The adaptor was brought to the surface of the bed with care to avoid axial compression. Samples to these columns were applied strictly through a superloop to minimize pre-column dispersion at the sample boundaries. Protein A media were packed in XK or TRICORN™ series columns (GE Healthcare). Experiments were run at 200 cm/hr. Column packing and chromatography experiments were conducted on an AKTA™ Explorer 100 (GE Healthcare).

In some anion exchange experiments, 500 mM NaCl was added to the sample to highlight the relative distribution of antibodies and salts. Experiments run at pH 3.0 were buffered with 50 mM citrate; at pH 4.0 with 50 mM acetate; at pH 5 with 25 mM acetate, 25 mM MES; at pH 6.0 with 50 mM MES; at pH 7.0 with 50 mM Hepes; at pH 8.0 with 50 mM Tris, at pH 9.0 and 10.0 with 50 mM borate. Purified IgG was prepared by applying filtered cell culture supernatant (CCS) to protein A affinity media equilibrated with 50 mM phosphate, 100 mM NaCl, pH 7.2. The column was washed after loading with equilibration buffer, then eluted with 100 mM arginine, 100 mM acetate, pH 3.5 (MABSELECT™) or 100 mM citrate, pH 3.0 (PROSEP™). In one experiment, initial purification of trastuzumab was conducted by cation exchange chromatography on POROS HSX. Cell culture supernatant titrated to pH 6.0 was diluted to a conductivity of 2.5 mS/cm, and loaded onto a column equilibrated with 50 mM MES, pH 6.0. This was followed by washing with equilibration buffer, then elution in a linear gradient to 50 mM MES, 200 mM NaCl, pH 6.0.

In one experiment, contaminating free light chain and light chain dimers remaining in trastuzumab after anion exchange processing of cell culture supernatant were removed by cation exchange chromatography as described above. In another experiment, light chain contaminants were removed by binding the sample to Capto adhere at 1 M NaCl, 50 mM Hepes, pH 7.0, then eluting with a descending linear gradient to 50 mM Hepes, pH 7.0. In another experiment, light chain contaminants were removed by binding the sample to hydroxyapatite in 50 mM Hepes, 5 mM sodium phosphate, pH 7.0, then eluting with a linear gradient to 1 M NaCl, 5 mM phosphate, pH 7.0, prior to cleaning with 500 mM phosphate, pH 7.0.

Antibody aggregates were monitored by size exclusion chromatography (SEC) on a Shimadzu HPLC system (Kyoto) with a G3000SWxl column (Tosoh Bioscience) equilibrated with 50 mM MES, 200 mM arginine, 5 mM EDTA, 0.05% sodium azide, pH 6.5) at 0.6 mL/min. 100 μL of sample was injected. Host cell proteins (HCP) were monitored by ELISA according to the manufacturer's recommendations with a CHO HCP kit from Cygnus Technologies Inc. (Southport, N.C.). Host Cell DNA was measured by intercalating dye assay according to manufacturer's recommendations with the ACCUBLUE High Sensitivity dsDNA Quantitation kit (Biotium, Inc., Hayward, Calif.). Endotoxin levels were measured by a standard kinetic chromogenic Limulus Amebocyte Lysate assay using ENDOSAFE ENDOCHROME-K™ LAL reagent (Charles River Laboratories Inc., Wilmington, Mass.). Infectivity testing for minute virus of mice (MVM) and murine leukemia virus (MuLV) was conducted by Charles River Laboratories (Cologne, Germany).

Trastuzumab Purification.

During the course of flow-through anion exchange chromatography of biosimilar trastuzumab (IgG) on UNOsphere Q, a well-defined shoulder was observed on the leading edge of the breakthrough fraction. Conductivity and pH of the shoulder matched the column equilibration conditions. Given the operating pH of 7.0 and the antibody isoelectric point (pI) of 8.45 it was concluded that the antibody was being repelled from the exchanger surface and forced to migrate exclusively through the void volume. When the column was loaded to 35% or less of its total volume, a single population of highly purified trastuzumab eluted entirely within the void volume, with good separation from the majority of contaminants as indicated in FIG. 1.

It was observed that peak width increased incrementally with NaCl concentration up to 4 M, but partitioning remained essentially complete. Partitioning was not observed at pH 9 and 10, which was attributed to the antibody's net charge reversal, but it was fully restored when the buffer included 50 mM or more NaCl. These results indicate that electrostatic repulsion was not necessary to achieve partitioning, instead partitioning appears to be dependent on suspending electrostatic attraction.

Figure 2:
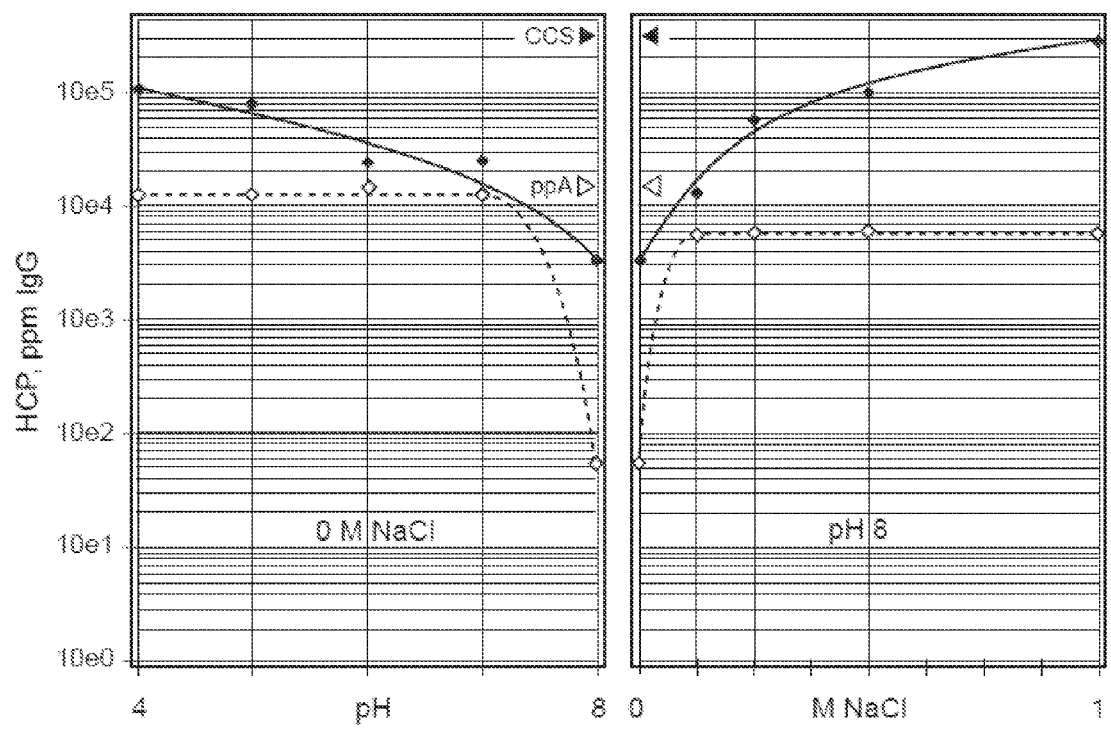
FIG. 2 shows plots indicating a reduction of host cell proteins by methods of the invention as a function of pH in the absence of NaCl (left panel), and as a function of salt concentration at pH 8.0 (right panel). Solid lines and black diamonds represent values from applied trastuzumab cell culture supernatant. Broken lines and open diamonds represent values from applied protein-A purified trastuzumab. Black triangles indicate host cell proteins in the cell culture supernatant before performing the method of the invention. Open triangles indicate host cell proteins in a protein A-purified sample.

Salts eluted after the void volume as indicated in FIG. 1. This provides a means of buffer exchanging the IgG into the equilibration buffer, and the collateral benefit of making partitioning independent of sample composition, even when IgG was applied in 3 M guanidine, pH 5.5. Since the majority of host cell proteins (HCP) are more acidic than IgG, host protein cell levels can be used as an index of non-IgG protein behavior. On columns equilibrated with 50 mM Tris, pH 8.0, the UNOSPHERE™ Q void volume partitioning removed 99.1% of host cell proteins from trastuzumab cell culture supernatant (CCS), 99.5% from ProSep protein A-purified IgG, and 99.6% from cation exchange-purified IgG. Host cell protein removal from cell culture supernatant declined with decreasing pH, and with increasing NaCl concentration of the equilibration buffer as indicated in FIG. 2.

UNOSPHERE™ Q void volume partitioning also achieved 99.5% DNA reduction from trastuzumab cell culture supernatant and protein A-purified trastuzumab at pH 7.0 and 8.0, at NaCl concentrations below 250 mM. Endotoxin was reduced 99.7% in 50 mM Hepes, 50 mM NaCl, pH 7.0. Viral infectivity testing of samples fractionated at the same conditions indicated a 3.5 log reduction Minute Virus of Mice (MVM), and a 3.0 log reduction of Murine Leukemia Virus (MuLV).

Figure 3:
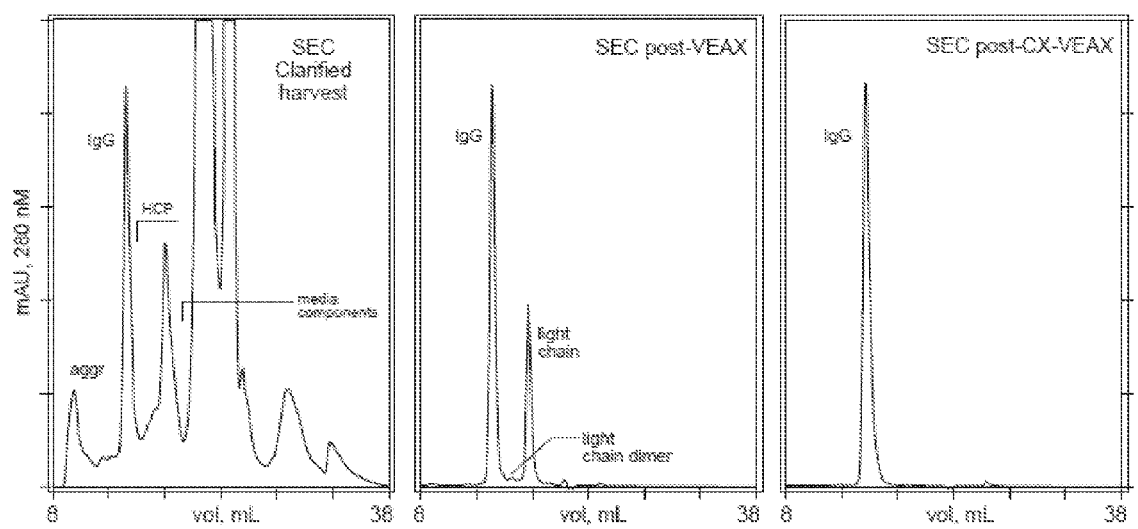
FIG. 3 shows analytical size exclusion chromatography (SEC) profiles of filtered trastuzumab from cell culture supernatant (left panel), void volume-fractionation of the cell culture supernatant (middle panel), and trastuzumab purified by cation exchange followed by void volume-partitioning (right panel).

In the UNOSPHERE™ Q void volume partitioning, trastuzumab co-eluted with free light chain and light chain dimers as indicated in FIG. 3 (middle panel). Light chain contaminants could be removed by hydroxyapatite with an ascending NaCl gradient, Capto adhere where the IgG was bound in 1 M NaCl and eluted in a descending salt gradient, and cation exchange chromatography with an ascending NaCl gradient. In a two-step procedure, cation exchange followed by UNOSPHERE™ Q void volume partitioning under column equilibration with 50 mM Tris, pH 8.0 reduced host cell proteins to 14 ppm, providing a reduction of 99.99% from cell culture supernatant, as indicated in FIG. 3 (right panel). Host cell protein content of the later eluting sample-salt-associated shoulder was about 678 ppm. IgG recovery was greater than 99%.

Other Antibody and Antibody Fragments.

Figure 4:
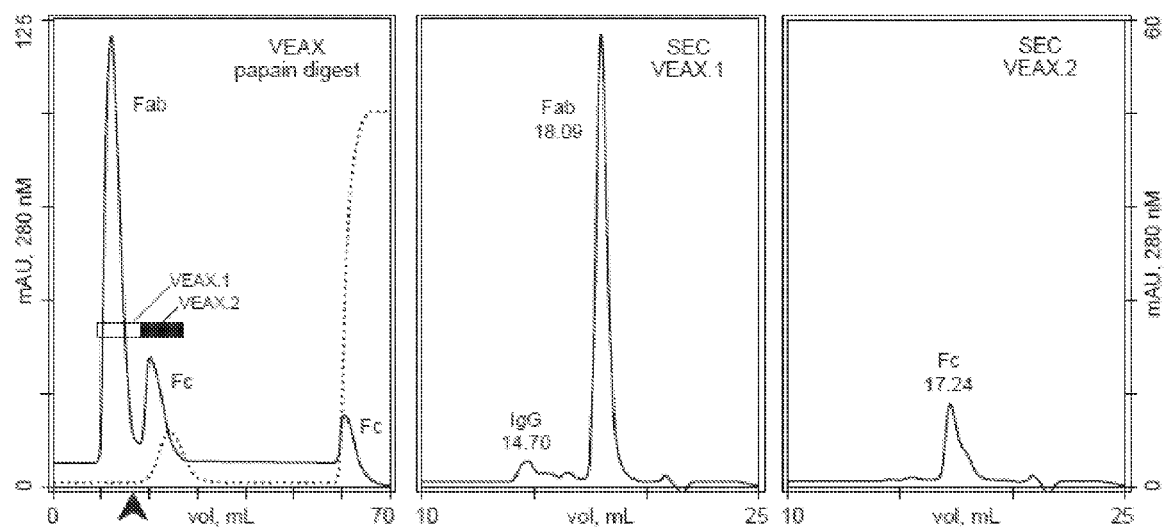
FIG. 4 shows analytical SEC profiles of the fractionation of papain-digested Rituxan, followed by analytical SEC profiles of the first and second peaks after void volume partitioning. Numerical values in the SEC profiles represent elution time in minutes. The solid line is UV absorbance. The broken line is conductivity.

Adalimumab (pI 8.25), and rituximab, partitioned via void volume partitioning as effectively as trastuzumab in 50 mM Tris, pH 8.0. Bevacizumab (pI 8.3) partitioned via void volume partitioning effectively in the presence of 100 mM NaCl, but not in the absence of salt. F(ab')2 derived from pepsin digestion of rituximab, and Fab from papain digestion partitioned via void volume partitioning as effectively as the intact antibody. With Fab, a second peak co-eluting with the sample-salt and a subsequent higher-salt elution peak proved to be residual Fc fragments as indicated in FIG. 4.

This observation is consistent with what is believed to be the underlying mechanism of the void volume partitioning because the Fc fragments from papain digests of rituximab were previously shown to contain a higher proportion of carboxyl groups than Fab. Without being bound by theory, it has been postulated that higher carboxyl content favors binding to anion exchange groups in the ligand-grafted exchanger media, and interferes with or prevents partitioning to the void volume. Fc fragments could be partitioned to the void with Fab in 200 mM NaCl, 50 mM Tris, pH 8.0, providing evidence that nullifying electrostatic attraction is an important factor in achieving partitioning.

Figure 5:
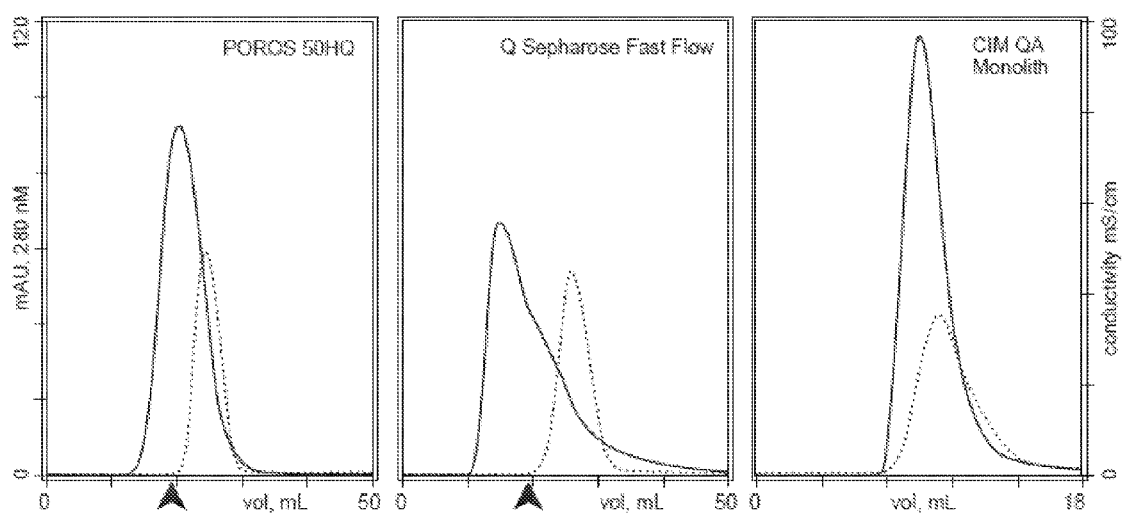
FIG. 5 shows SEC profiles indicating compromised antibody partitioning by anion exchangers unsuitable for void volume partitioning. QFF: Q Sepharose Fast Flow. FDHC: Fractogel DEAE HighCap. P50HQ: POROS 50 HQ. The solid line is UV absorbance. The broken line is conductivity.

Given that void volume partitioning depends, in part, on the size exclusion characteristics of a low density polymer zone in packed porous particles, it was expected that anion exchangers lacking this feature would not perform well in void volume partitioning. This was indicated with Q Sepharose Fast Flow, which is typically understood to embody a monolayer of charged groups on an openly accessible pore surface. Only about 65% of trastuzumab partitioned to the void volume, with most of the remainder co-eluting with the residual salt from the applied sample as indicated in FIG. 5 (left panel). A perfusive particle anion exchanger supported less than 50% partitioning. This observation may reflect difference in grafting or alternatively, the influence of convective channels transecting the particles. Membrane and monolithic anion exchangers also did not perform well, which is believed to be because they lack a void volume for the antibody to be excluded into. Fractogel DEAE HiCap achieved about 75% partitioning as indicated in FIG. 5 (middle panel). GigaCap Q achieved about 85% partitioning; CAPTO Q about 95%. Complete partitioning was achieved by Nuvia Q and UNOSPHERE Q (FIG. 1), with the latter supporting the best separation between the IgG and sample-salt peaks. These observations with various exchangers indicate that grafting may have a general effect of imposing size exclusion limitations on biomolecules lacking a strong electrostatic attraction to the exchanger.

The pH of a trastuzumab MAbSelect protein A eluate was titrated to pH 7.0 and then applied 6.5 mL to a 20 mL column of UNOsphere Q equilibrated to 50 mM Tris, pH 8.0. Another aliquot was separately diluted about 4.5-fold with water to achieve a conductivity of 5 mS/cm, then flowed sample amounting to 100 mg of IgG over a 1 mL column of UNOsphere Q equilibrated to 50 mM Tris, 50 mM NaCl, pH 8.0. HCP was reduced to 2 ppm by void volume partitioning, and to 3 ppm by flow-through. While void volume partitioning employed a larger volume of both buffer and chromatography media per unit of antibody, it also produced the unexpected benefit of reducing aggregates from 0.45% to less than 0.05%, where flow-through reduced them to only 0.35%.

Figure 6:
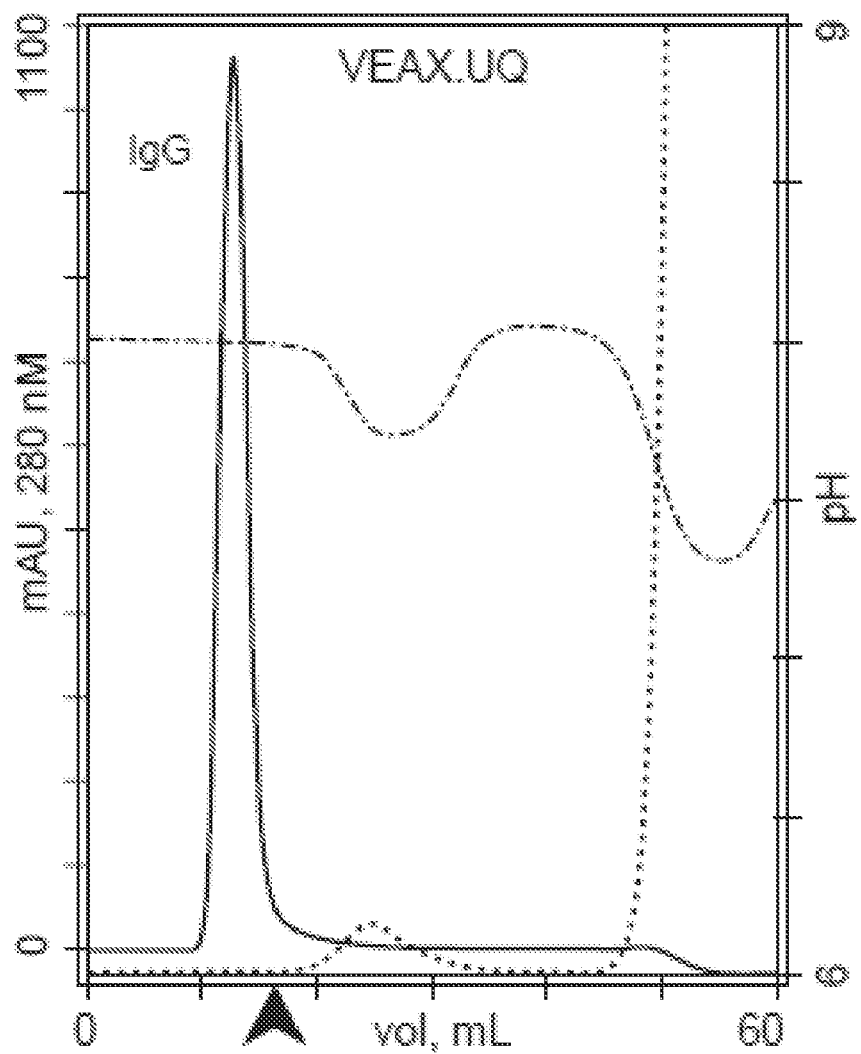
FIG. 6 shows a plot of pH excursions as a function of salt concentration. UNOsphere Q equilibrated to 50 mM Tris, pH 8.0. Protein A-purified trastuzumab. Solid line: UV absorbance. Simple broken line: conductivity. Compound broken line: pH. The conductivity peak beginning at about 13 mL is from salts in the applied antibody sample. The conductivity increase beginning at about 45 mL corresponds with a 2.0 M NaCl cleaning step.

Methods of the invention employing void volume partitioning may provide the additional benefit that such methods support better process control than other anion exchange formats. For example, uncontrolled pH excursions during ion exchange processes have been noted in the art. Increases in salt concentration displace buffering counterions such as $H^+$ or $OH^-$ from ion exchange surfaces and can create uncontrolled increases or decreases in pH. Such excursions may exceed 2 pH units in amplitude and persist for several column volumes. Decreases in salt concentration mediate similar effects, with the opposite sign. In typical flow-through anion exchange, changes in salt concentration occur at the beginning and end of the sample load. Their influence may be tolerated in some cases, but still represents loss of control for a primary process variable. In methods of the invention employing void volume partitioning, salts trail behind the antibody, so pH excursions do not occur until after the IgG has eluted from the column as shown in the plot of FIG. 6. This delay in salt elution and the resultant pH excursion may contribute to both better performance and better reproducibility.

The methods disclosed herein and exemplified in the Examples indicate an ability to reduce greater than 99% of host proteins, DNA, and endotoxin contaminants. Virus contaminant can be reduced more than 99.9%, and aggregates can be generally reduced to less than 0.05%. The combination of a tolerance for a wide range of sample conditions and achieving buffer exchange in conjunction with a high degree of contaminant removal increases the flexibility and utility of ligand-grafted anion exchange chromatography media as a tool for antibody purification.

The present invention may be combined with other purification methods to achieve higher levels of purification. Examples of such other purification methods include, but are not limited to, other methods commonly used for purification of IgG, such as protein A and other forms of affinity chromatography, anion exchange chromatography, cation exchange chromatography, hydrophobic interaction chromatography, immobilized metal affinity chromatography, and additional mixed mode chromatography methods; also methods of precipitation, crystallization, and liquid-liquid extraction. It is within the purview of a person of ordinary skill in the art to develop appropriate conditions for the various methods and integrate them with the invention herein to achieve the necessary purification of a particular antibody.

All references cited herein are incorporated by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, chromatography conditions, and so forth used in the specification and claims are to be understood as being modified in all instances by the term "about." Accordingly, unless indicated to the contrary, the numerical parameters set forth in the specification and attached claims are approximations that may vary depending upon the desired performance sought to be obtained by the present invention.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

The invention claimed is:

1. A method of purifying a sample containing a desired protein comprising: (i) providing a packed chromatographic column comprising positively charged porous particles, wherein the positively charged porous particles comprise anion exchange particles; (ii) equilibrating the column to the conditions to which the desired protein in the sample is to elute; (iii) contacting the sample with the column such that a volume of the sample applied to the column consists of a volume that is less than or equal to a void volume of the positively charged porous particles within the column; and (iv) collecting the column effluent from the column, wherein the column effluent comprises the desired protein, the desired protein is in a purer state and in the conditions to which the column was equilibrated, and the desired protein is an IgG antibody, IgG antibody fragment, IgG antibody derivative, or IgG antibody fusion protein.

2. The method of claim 1 wherein the desired protein is an IgG antibody.

3. The method of claim 1 wherein the desired protein is derived from an IgG antibody in a form selected from the group consisting of a Fab fragment, a F(ab')2 fragment, a minibody, a diabody, a VHH domain, an Fc-fusion protein, or an IgG derivative having charge properties similar to that of an IgG antibody.

4. The method of claim 1, wherein the sample may be unpurified, at an intermediate level of purity, or highly purified.

5. The method of claim 1, wherein the sample volume is less than 99% of the void volume of the positively charged porous particles within the column.

6. The method of claim 5, wherein the sample volume is less than 95% of the void volume of the positively charged porous particles within the column.

7. The method of claim 6, wherein the sample volume is less than 90% of the void volume of the positively charged porous particles within the column.

8. The method of claim 7, wherein the sample volume is less than 80% of the void volume of the positively charged porous particles within the column.

9. The method of claim 8, wherein the sample volume is less than 70% of the void volume of the positively charged porous particles within the column.

10. The method of claim 9, wherein the sample volume is less than 10% of the void volume of the positively charged porous particles within the column.

11. The method of claim 10 wherein the sample volume is less than 5% of the void volume of the positively charged porous particles within the column.

12. The method of claim 1 wherein the column is packed solely with positively charged porous particles and the sample volume is less than 40% of the volume of the packed column.

13. The method of claim 1 wherein the column is equilibrated to a pH between approximately 4 and approximately 9.

14. The method of claim 1 wherein the column is equilibrated to a conductivity value between approximately 0.1 mS/cm and approximately 30 mS/cm.

15. The method of claim 1, wherein the column is equilibrated with a buffer having a pH in a range selected from the group consisting of (1) from about 6.5 to about 8.5, (2) from about 6.5 to about 7.5, and (3) from about 7.5 to about 8.5.

16. The method of claim 1 wherein the column is equilibrated to a conductivity value between about 0.1 and about 15 mS/cm.

17. The method of claim 1, wherein the sample comprises a pH in a range from a pH of approximately 2 to a pH of approximately 10.

18. The method of claim 1 wherein the sample comprises a conductivity in a range from approximately 0.1 mS/cm to approximately 250 mS/cm.

19. The method of claim 1, wherein the conditions to which the column is equilibrated comprise a pH in a range from a pH of approximately 4 to a pH of approximately 9.

20. The method of claim 1 wherein the conditions to which the column is equilibrated comprise a conductivity in a range from approximately 0.1 mS/cm to approximately 30 mS/cm.

21. The method of claim 1 wherein the anion exchange particles possess an electropositivity, at least of portion of the electropositivity being provided by a moiety selected from the group consisting of tris(2-aminoethyl)amine, polyarginine, polylysine, polyethyleneimine, polyallylamine, diethyleneaminoethyl, ethylene diamino, a primary amino moiety, a secondary amino moiety, a tertiary amino moiety, and a quaternary amino moiety.

22. The method of claim 1 comprising the additional step of contacting the sample with an aggregate-dissociating agent prior to the step of contacting the sample with the column.

23. The method of claim 22 wherein the aggregate-dissociating agent is an organic cation.

24. The method of claim 23 wherein the organic cation is selected from the group consisting of ethacridine, 9-aminoacridine (aminacrine), 3,6 acridinediamine (proflavin), acrisorcin, acrizane (phenacridane), acridine orange, quinacrine, acricide, acridone, acridine-9-carboxylic acid, acranil (1-[(6-chloro-2-methoxy-9-acridinyl)amino] 3-(diethylamino)-2-propanol dihydrochloride), phenosafranin, phenoxazine, phenothiazine, acriflavine (3,6-diamino-10-methylacridinium, chloride and 3,6-acridineidiamine), arginine, and chlorhexidine.

25. The method of claim 24 wherein the organic cation is ethacridine, chlorhexidine, arginine, or a salt thereof.

26. The method of claim 25 wherein the organic cation is ethacridine or a salt thereof.

27. The method of claim 24 wherein the organic cation is present in an amount between approximately 0.01% and approximately 0.05%.

28. The method of claim 24 wherein the organic cation is present in an amount less than approximately 0.01%.

29. The method of claim 24 wherein the organic cation is present in an amount less than approximately 0.005%.

30. The method of claim 24 wherein the organic cation is present in an amount less than approximately 0.001%.

31. The method of claim 24 wherein the organic cation is present in an amount between approximately 0.020 and approximately 0.025%.

32. The method of claim 24 wherein the sample is treated with more than one organic cation selected from the group consisting of ethacridine, arginine, and chlorhexidine and salts thereof prior to the step of contacting the sample with the column.

33. The method of claim 32 wherein the organic cations used to treat the sample prior to the step of contacting the sample with the column are provided in a concentration of less than 1%.

34. The method of claim 32 wherein the organic cations used to treat the sample prior to the step of contacting the sample with the column are provided in a concentration between approximately 0.01% and approximately 0.05%.

35. The method of claim 32 wherein the organic cations used to treat the sample prior to the step of contacting the sample with the column are provided in a concentration less than approximately 0.01%.

36. The method of claim 32 wherein the organic cations used to treat the sample prior to the step of contacting the sample with the column are provided in a concentration less than approximately 0.005%.

37. The method of claim 32 wherein the organic cations used to treat the sample prior to the step of contacting the sample with the column are provided in a concentration less than approximately 0.001%.

38. The method of claim 32 wherein the organic cations used to treat the sample prior to the step of contacting the sample with the column are provided in a concentration between approximately 0.020 and approximately 0.025%.

39. The method of claim 23, wherein the sample is additionally contacted with a soluble organic modulator selected from the group consisting of nonionic organic polymers, organic solvents, surfactants, and ureides, prior to the step of contacting the sample with the column.

40. The method of claim 39 wherein the step of contacting the sample with the organic modulator occurs prior to the step of contacting the sample with the organic cation.

41. The method of claim 39 wherein the step of contacting the sample with the organic modulator occurs substantially simultaneously with the step of contacting the sample with the organic cation.

42. The method of claim 39 wherein the step of contacting the sample with the organic modulator occurs after the step of contacting the sample with the organic cation.

43. The method of claim 39 wherein the organic modulator is a nonionic organic polymer selected from the group consisting of polyethylene glycol, polypropylene glycol and polybutylene glycol.

44. The method of claim 43 wherein the nonionic organic polymer has an average molecular weight of approximately 500 D or less.

45. The method of claim 39 wherein the organic modulator is an organic solvent selected from the group consisting of ethylene glycol, propylene glycol, butylene glycol, dimethylsulfoxide, ethanol, isopropanol, and phenoxyethanol.

46. The method of claim 39 wherein the organic modulator is provided at a concentration of approximately 1% (w/v) or greater.

47. The method of claim 39 wherein the organic modulator is a surfactant selected from the group consisting of Tween, triton, CHAPS, CHAPSO and octyl glucoside.

48. The method of claim 47 wherein the surfactant is provided at a concentration of approximately 1% (w/v) or less.

49. The method of claim 47 wherein the surfactant is provided at a concentration of approximately 0.1% (w/v) or less.

50. The method of claim 39 wherein the organic modulator is a ureide provided in a subsaturating amount.

51. The method of claim 50 wherein the ureide is selected from the group consisting of urea, hydantoin, and allantoin.

52. The method of claim 1 wherein the sample is additionally contacted with an antiviral agent, prior to the step of contacting the sample with the column.

53. The method of claim 52 wherein the antiviral agent is an non-multivalent organic cation with at least one positive charge.

54. The method of claim 52 wherein the antiviral agent lacks a positive charge.

55. The method of claim 52 wherein the antiviral agent is present in an amount less than approximately 1% (w/v).

56. The method of claim 55 wherein the antiviral agent is present in an amount less than approximately 0.1% (w/v).

57. The method of claim 56 wherein the antiviral agent is present in an amount less than approximately 0.01% (w/v).

58. The method of claim 57 wherein the antiviral agent is present in an amount less than approximately 0.001% (w/v).

59. The method of claim 1 comprising the additional steps of, prior to the step of contacting the sample with the column, contacting the sample with a ureide in an amount sufficient for the ureide to be supersaturated in the sample, and separating the supernatant containing the desired protein from the solid or undissolved portions of the sample.

60. The method of claim 59 wherein the step of contacting the sample with the ureide occurs prior to the step of contacting the sample with the organic cation.

61. The method of claim 59 wherein the step of contacting the sample with the ureide occurs substantially simultaneously with the step of contacting the sample with the organic cation.

62. The method of claim 59 wherein the step of contacting the sample with the ureide occurs after the step of contacting the sample with the soluble organic cation of mixed chemical character.

63. The method of claim 59 wherein the ureide is selected from the group consisting of urea, uric acid, hydantoin, allantoin, alcloxa, aldioxa, hemocane, ureidohydantoin, 5-ureidohydantoin, glyoxylureide, glyoxylic acid diureide, 2,5-dioxo-4 imidazolidinyl urea, and punnes.

64. The method of claim 63 wherein the ureide is allantoin.

65. The method of claim 63 wherein the ureide is uric acid.

66. The method of claim 64 wherein the allantoin is present in an amount greater than 0.5% (w/v).

67. The method of claim of claim 66 wherein the allantoin is present in an amount greater than approximately 1% (w/v).

68. The method of claim 65 wherein the uric acid is present in an amount greater than 0.0025% (w/v).

69. The method of claim 68 wherein the uric acid is present in an amount greater than approximately 0.01% (w/v).

70. The method of claim 68 wherein the uric acid is present in an amount greater than approximately 0.1% (w/v).

71. The method of claim 68 wherein the uric acid is present in an amount greater than approximately 1% (w/v).

72. The method of claim 1 comprising the additional step of removing insoluble solids prior to the step of contacting the sample with the column.

73. The method of claim 72 wherein the step of removing insoluble solids is performed after the step or steps of one or more of contacting the sample with an organic modulator, antiviral agent or supersaturated ureide.

74. The method of claim 39 wherein, after the step or steps of one or more of contacting the sample with an organic modulator or ureide, the sample is contacted with a solid material having chemical moieties capable of adsorbing at least some of the organic modulators and ureides added to the sample.

75. The method of claim 74, wherein the solid material is composed of particles added to the sample and subsequently separated from the sample.

76. The method of claim 74 wherein the solid material is composed of a membrane, a monolith, or column packed with particles through or across which the sample is passed.

77. The method of claim 74, wherein the chemical moieties on the solid materials may include one or more of groups having the capacity for cation exchange, anion exchange, hydrophobic interactions, hydrogen bonding, pi-pi interactions, or metal chelation.

78. The method of claim 74 comprising the additional step of separating from or removing insoluble solids from the sample after the step of contacting the sample with the solid material having chemical moieties capable of adsorbing at least some of the organic modulators, antiviral agents and ureides added to the sample and prior to the step of contacting the sample with the column.

79. The method of claim 1 wherein the sample contains aggregates wherein the purer state of the desired protein has a reduced aggregate content in comparison with the sample.

80. The method of claim 79 wherein the aggregates comprise homo-aggregates of the desired protein.

81. The method of claim 80 wherein the presence of homo-aggregates of the desired protein in the sample is substantially eliminated.

82. The method of claim 79 wherein the aggregates comprise hetero aggregates of the desired protein and a contaminant.

83. The method of claim 82 wherein the hetero-aggregates are of substantially the same hydrodynamic size as the desired protein.

84. The method of claim 82 wherein the contaminant is a nucleic acid, nucleotide, endotoxin, metal ion, protein, lipid, or cell culture media component.

85. The method of claim 82 wherein the presence of hetero-aggregates of the desired protein and a contaminant is substantially eliminated.

86. The method of claim 1 wherein the sample contains one or more contaminants wherein the purer state of the desired protein has a reduced content of such contaminants in comparison with the sample.

* * * * *